(12) United States Patent
Lefebvre et al.

(10) Patent No.: US 11,972,871 B2
(45) Date of Patent: Apr. 30, 2024

(54) SIMULATING EVOLUTION OF A TUMOR

(71) Applicant: DASSAULT SYSTEMES, Velizy Villacoublay (FR)

(72) Inventors: Guillaume Lefebvre, Velizy-Villacoublay (FR); Arthur Ball, Velizy-Villacoublay (FR); Nicolas Pecuchet, Velizy-Villacoublay (FR); Marine Zulian, Biot (FR)

(73) Assignee: DASSAULT SYSTEMES, Velizy Villacoublay (FR)

( * ) Notice: Subject to any disclaimer, the term of this patent is extended or adjusted under 35 U.S.C. 154(b) by 1152 days.

(21) Appl. No.: 16/504,158

(22) Filed: Jul. 5, 2019

(65) Prior Publication Data
US 2020/0027564 A1 Jan. 23, 2020

(30) Foreign Application Priority Data

Jul. 4, 2018 (EP) .................................... 18305878

(51) Int. Cl.
*G16H 50/50* (2018.01)
*G16B 5/20* (2019.01)

(52) U.S. Cl.
CPC ............... *G16H 50/50* (2018.01); *G16B 5/20* (2019.02)

(58) Field of Classification Search
None
See application file for complete search history.

(56) References Cited

U.S. PATENT DOCUMENTS

2016/0103971 A1  4/2016  Hillis et al.

OTHER PUBLICATIONS

Ribba, Benjamin, Thierry Colin, and Santiago Schnell. "A multiscale mathematical model of cancer, and its use in analyzing irradiation therapies." Theoretical Biology and Medical Modelling 3 (2006): 1-19.*
Relling, Mary V., and William E. Evans. "Pharmacogenomics in the clinic." Nature 526.7573 (2015): 343-350.*
Japanese Office Action dated Apr. 25, 2023 in Japanese Patent Application No. 2019-125359 (with unedited computer-generated English translation), 12 pages.
Atsushi Niida, Koshi Mimori & Satoru Miyano, "Intratumor heterogeneity and cancer evolution", [online], Japan, Feb. 19, 2016, p. 1-9, [Apr. 14, 2023 search], Retrieved from the Internet <URL:https://dbarchive.biosciencedbc.jp/data/leading_authors/data/Doc/Miyano-5.e003-PDF.pdf>.
Office Action dated Feb. 4, 2024, issued in counterpart CN Application No. 201910611371.6 filed on Jul. 4, 2019, with English Translation. (25 pages).
Office Action issued Dec. 21, 2018, in European Patent Application No. 18305878.3-1126; pp. 1-10. (10 pgs.).
Le Zhang, et al.; "Development of a three-dimensional multiscale agent-based tumor model: Simulating gene-protein interaction profiles, cell phenotypes and multicellular patterns in brain cancer"; Journal of Theoretical Biology 244 (2007); pp. 96-107; 12 pgs.
S. Ammari, et al.; "Radiological evaluation of response to treatment: Application to metastatic renal cancers receiving anti-angiogenic treatment"; Diagnostic and Interventional Imaging (2014) 95; pp. 527-539; 13 pgs.
Alexander R.A. Anderson, et al.; "Tumor Morphology and Phenotypic Evolution Driven by Selective Pressure from the Microenvironment"; Cell 127; Dec. 1, 2006; pp. 905-915; 11 pgs.
Mollie E. Barnard, et al.; "Established breast cancer risk factors and risk of intrinsic tumor subtypes"; Article in Press; Biochimica Et Biophysica ACTA (2015); Reviews on Cancer; pp. 1-13; 13 pgs.
Niamh E. Buckley, et al.; "Quantification of HER2 heterogeneity in breast cancer-implications for identification of sub-dominant clones for personalized treatment"; Scientific Reports; Mar. 2016; pp. 1-8; 8 pgs.
F. Cardoso, et al.; "$3^{rd}$ ESO-ESMO International Consensus Guidelines for Advanced Breast Cancer (ABC 3)"; Annals of Oncology 28: 2017; Published Online Dec. 5, 2016; vol. 28; Issue 1; 2017; pp. 16-33; 18 pgs.
P. H. Cottu, et al.; "Intratumoral heterogeneity of HER2/neu expression and its consequences for the management of advanced breast cancer"; Annals of Oncology 19: 2018; 2008 European Society for Medical Oncology; downloaded from https://academic.oup.com/annonc/article-abstract/19/3/595/248015 by INSERM user on Mar. 23, 2018; pp. 596-597; 2 pgs.
Mitch Dowsett, et al.; "Disease-Free Survival According to Degree of HER2 Amplification for Patients Treated With Adjuvant Chemotherapy With or Without 1 Year of Trastuzumab: The HERA Trial"; Journal of Clinical Oncology; vol. 27, No. 18; Jun. 20, 2009; pp. 2962-2969; 8 pgs.
Anthony Ferrari, et al.; "A whole-genome sequence and transcriptome perspective on HER2-positive breast cancers"; Nature Communications Article; Published Jul. 13, 2016; pp. 1-9; 9 pgs.
Watal M. Iwasaki, et al.; "Simulation framework for generating intratumor heterogeneity patterns in a cancer cell population"; PLOS One Research Article; Published Sep. 6, 2017; pp. 1-28; 28 pgs.

(Continued)

*Primary Examiner* — G. Steven Vanni
(74) *Attorney, Agent, or Firm* — Oblon, McClelland, Maier & Neustadt, L.L.P.

(57) ABSTRACT

The disclosure notably relates to a computer-implemented method for simulating evolution of a tumor associated to an oncogene. The method includes providing a plurality of pieces of data, each corresponding to a given cell of the tumor, and includes a degree of activation of the oncogene in the given cell. The method further includes providing a model configured to take an input piece of data and to output information on proliferation of the respective given cell corresponding to the input piece of data. The information on proliferation depends on the degree of activation of the oncogene. The method further includes running the model on one or more pieces of data of the plurality of pieces of data and updating the plurality of pieces of data based on the result of the running. Such a method improves the simulation of the evolution of a tumor.

14 Claims, 15 Drawing Sheets

(56) References Cited

OTHER PUBLICATIONS

Guillaume Lefebvre, et al.; "Spatial modelling of tumour drug resistance: the case of GIST liver metastases"; Mathematical Medicine and Biology Advance Access; Published Mar. 31, 2016; pp. 1-26; 26 pgs.
Neal I. Lindeman, et al.; "Molecular Testing Guideline for Selection of Lung Cancer Patients for EGFR and ALK Tyrosine Kinase Inhibitors"; The Journal of Molecular Diagnostics; vol. 15, No. 4; Jul. 2013; pp. 415-453; 39 pgs.
Michael Marotta, et al.; "Palindromic amplification of the ERBB2 oncogene in primary HER2-positive breast tumors"; Scientific Reports; Published Feb. 17, 2017; pp. 1-12; 12 pgs.
Michael Marotta, et al.; "A common copy-number breakpoint of ERBB2 amplification in breast cancer colocalizes with a complex block of segmental duplications"; Breast Cancer Research 2012; Research Article; Nov. 2012; pp. 1-19; 20 pgs.
Hiroaki Nitta, et al.; "The assessment of HER2 status in breast cancer: the past, the present, and the future"; Pathology International 2016; Review Article; pp. 313-324; 12 pgs.
S. Novello, et al.; "Metastatic non-small-cell lung cancer: ESMO Clinical Practice Guidelines for diagnosis, treatment and follow-up"; Annals of Oncology 27; Sep. 2016; page rage is not indicated; 27 pgs.
Katie M. O'Brien, et al.; "Breast Cancer Subtypes and Previously Established Genetic Risk Factors: A Bayesian Approach"; Research Article; Published Online First; Oct. 31, 2013; pp. 84-97; 15 pgs.
Jan Poleszczuk, et al.; "Evolution and Phenotypic Selection of Cancer Stem Cells"; Research Article; PLOS Computational Biology; Published Mar. 5, 2015; pp. 1-14; 14 pgs.
Benjamin Ribba, et al.; "A multiscale mathematical model of cancer, and its use in analyzing irradiation therapies"; Theoretical Biology and Medical Modelling; Published Feb. 10, 2006; pp. 1-19; 19 pgs.
Andrea Sottoriva, et al.; "A Bing Bang model of human colorectal tumor growth"; HHS Public Access; Author Manuscript; Nat Genet.; Available in PMC; Sep. 19, 2015; pp. 1-22; 22 pgs.
Jane Starczynski, et al.; "A Rogues' Gallery of Challenging Diagnostic Cases: UKNEQAS Interpretation Guidelines and Research Recommendations"; Anatomic Pathology/HER2 Gene Amplification in Breast Cancer; 2012; retrieved on Mar. 23, 2018; pp. 595-605; 11 pgs.
Bartlomiej Waclaw, et al.; "A spatial model predicts that dispersal and cell turnover limit intratumour heterogeneity"; NHS Public Access Author Manuscript; Available in PMC; Mar. 8, 2016; pp. 1-29; 29 pgs.
Takaaki Watanabe, et al.; "Model Systems Facilitating an Understanding of Mechanisms for Oncogene Amplification"; Published By Intech; World's Largest Science, Technology & Medicine Open Access Book Publisher; Chapter 9; 2013; pp. 210-224; 17 pgs.
Antonio C. Wolff, et al.; "Recommendations for Human Epidermal Growth Factor Receptor 2 Testing in Breast Cancer: American Society of Clinical Oncology/College of American Pathologists Clinical Practice Guideline Update"; Journal of Clinical Oncology—ASCO Special Article; vol. 31, No. 31; Nov. 1, 2013; pp. 3977-4013; 18 pgs.
Timothy A. Yap, et al.; "Intratumor Heterogeneity: Seeing the Wood for the Trees"; www.sciencetranslationmedicine.org; vol. 4, Issue 127; Mar. 28, 2012; pp. 1-5; 5 pgs.

\* cited by examiner

SIMULATING EVOLUTION OF A TUMOR

CROSS-REFERENCE TO RELATED APPLICATIONS

This application claims priority under 35 U.S.C. § 119 or 365 to European Application No. 18305878.3, filed Jul. 4, 2018. The entire contents of the above application(s) are incorporated herein by reference.

FIELD OF THE INVENTION

The invention relates to the field of computer programs and systems, and more specifically to a method, system and program for simulating evolution of a tumor.

BACKGROUND

Computer-implemented methods exist for simulating evolution of a tumor. With the increase in computing resources, these methods allow to study the dynamics of tumors and thus form an important tool as well as a source of information for the medical field.

Some of these methods are based on solving partial differential equations. These methods allow the simulation of tumors in specific locations and describe the tumor behavior at the tissue scale. However, although such models can describe tumors, their accuracy is relatively low.

Within this context, there is still a need for an improved method for simulating the evolution of a tumor.

SUMMARY OF THE INVENTION

It is therefore provided a computer-implemented method for simulating the evolution of a tumor. The tumor is associated to an oncogene. The method comprises providing a plurality of pieces of data. Each piece of data corresponds to a given cell of the tumor. Each piece of data includes a degree of activation of the oncogene in the given cell corresponding to a respective piece of data. The method further comprises providing a model. The model is configured to take an input piece of data. The model is further configured to output an information on proliferation of the respective given cell corresponding to the input piece of data. The information on proliferation depends on the degree of activation of the oncogene in the respective given cell. The method further comprises running the model on one or more pieces of data of the plurality of pieces of data. The model further comprises updating the plurality of pieces of data based on the result of the running.

The method may comprise one or more of the following:
  each piece of data further includes a spatial localization of the given cell of the tumor;
  the information on proliferation of the respective given cell includes an information relative to presence or absence of division of the respective given cell, and when the information on proliferation of the respective given cell includes information relative to presence of division, the information on proliferation of the respective given cell further includes, for each cell resulting from the division, an information on a respective spatial localization, each respective spatial localization being in a neighborhood of the spatial localization of the respective given cell;
  the information on proliferation of the respective given cell further depends on space availability in the neighborhood of the respective given cell;
  the information relative to presence or absence of division of the respective given cell is based on the space availability in the neighborhood of the respective given cell, and when the information on proliferation of the respective given cell includes information relative to presence of division, the respective spatial localization in the neighborhood of the spatial localization of the respective given cell is at an unoccupied spatial localization;
  when the information on proliferation of the respective given cell includes information relative to presence of division, the information on proliferation of the respective given cell further includes for each cell resulting from the division, a respective degree of activation of the oncogene, based on the degree of activation of the oncogene of the respective given cell;
  the respective degree of activation of the oncogene of each cell resulting from the division corresponds to an at least partly probabilistic variation of the degree of activation of the oncogene of the respective given cell;
  the model is decision-based and includes, relative to the respective given cell a decision on death or survival, a decision on absence or presence of division, and a decision on acquisition of one or more new alterations during a division;
  providing a treatment type, the information on proliferation depending on the treatment type;
  the providing, the running and the updating are iterated, and the provided plurality of pieces of data of each iteration is the updated plurality of pieces of data of the previous iteration;
  providing data relative to a patient having the tumor, the model comprising parameters that depend on the data relative to the patient;
  providing the model comprises determining the parameters as values configured for retrieving the plurality of pieces of data by defining one or more other pieces of data, each other piece of data corresponding to a given cell of an initial state of the tumor, each other piece of data including a degree of activation of the oncogene in the given cell, running the model on one or more other pieces of data, and updating the plurality of other pieces of data based on the result of the running;
  optionally the values parameters are initialized based on the data relative to the patient; and/or
  determining a statistic relative to the oncogene, based on the updated plurality of pieces of data.

It is further provided a computer program comprising instructions for performing the method.

It is further provided a data structure including the model. In other words, the data structure includes specifications of a model configured to take an input piece of data corresponding to a given cell of a tumor and including a degree of activation, in the given cell, of an oncogene associated to the tumor. The model is further configured to output an information on proliferation of the given cell, the information on proliferation depending on the degree of activation of the oncogene in the given cell. The model is further configured to be run.

It is further provided a computer readable storage medium having recorded thereon the computer program and/or the data structure including the model.

It is further provided a system comprising a processor coupled to a memory and a graphical user interface, the memory having recorded thereon the computer program and/or the data structure including the model.

BRIEF DESCRIPTION OF THE DRAWINGS

Embodiments of the invention will now be described, by way of non-limiting example, and in reference to the accompanying drawings, where.

DETAILED DESCRIPTION OF THE INVENTION

Figure 1:
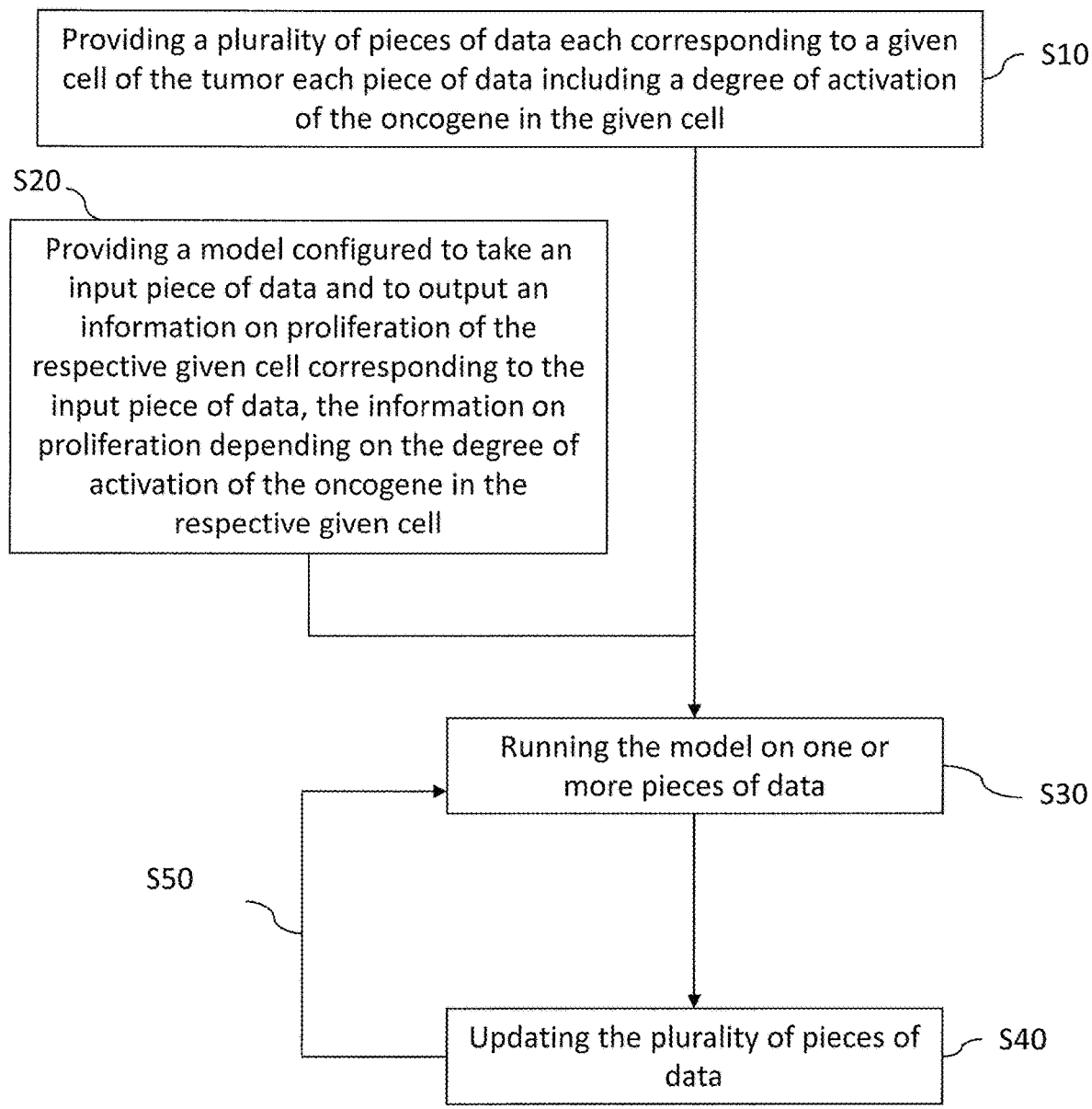
FIG. 1 shows a flowchart of an example of the method.

With reference to the flowchart of FIG. 1, it is proposed a computer-implemented method for simulating the evolution of a tumor associated to an oncogene. The method comprises providing S10 a plurality of pieces of data. Each piece of data is information stored in the computer which corresponds to a given cell of the tumor. Each piece of data includes a degree of activation of the oncogene in the given cell. The method also comprises providing S20 a model configured to take as an input a piece of data. The model is further configured to output an information on the proliferation of the respective given cell which corresponds to the input piece of data. The information on proliferation depends on the degree of activation of the oncogene in the respective given cell. The method further comprises running S30 the model on one or more pieces of data, the pieces of data being part of the plurality of pieces of data. The method further comprises updating S40 the plurality of pieces of data based on the result of the model run.

Such a method improves the simulation of the evolution of a tumor.

Notably, the method simulates the evolution of a tumor by computing at S30 the proliferation of one or more cells and updating at S40 the plurality of pieces of data provided at S10 based on the result of S30.

Thanks to providing at S20 a model configured to output proliferation information depending on a degree of activation of the oncogene, the model takes into account said degree of activation of the oncogene when simulating how the cells proliferate. This improves accuracy of the simulation of the evolution of the tumor. Indeed, how cells proliferate is affected by the degree of activation of the oncogene inside the cells. For example, the rate of division of a cell may increase as the degree of activation of the oncogene inside such a cell increases.

Thanks to the outputted proliferation information of a cell corresponding to a piece of data used as input of the model depending on the degree of activation of the oncogene in said cell, the simulation of the evolution of the tumor takes into account information at the cell level. This yet improves accuracy.

Thanks to each piece of data from the plurality of pieces of data including a degree of activation of the oncogene in the corresponding cell, and the updating S40 of the plurality of pieces of data being based on the result of the run S30, each piece of data of the updated plurality of pieces of data includes a degree of activation of the oncogene in their respective cell. Therefore, the intra-tumor heterogeneity related to the degree of activation of the oncogene in different cells is maintained throughout the simulation. This yet improves accuracy of the simulation. Indeed, cancers are heterogeneous diseases and knowledge on the intra-tumor heterogeneity increases the accuracy of diagnostics and therapeutics, such as in breast cancer.

The evolution of a tumor is how the tumor develops in time. For example, the size of a tumor may increase as time goes by and the tumor cells divide. Alternatively, the tumor may decrease in size if the patient which has the tumor undergoes treatment. Additionally or alternatively, the evolution of the tumor may comprise the evolution of the cells of the tumor, such as acquisition of resistance to certain treatments by one or more cells and/or changes in the level of activation of one or more oncogenes in one or more cells.

The tumor is associated to an oncogene. Thus, the oncogene may be active in at least one cell of the tumor. The oncogene inside such cell may have varying degrees of activation. In examples, the degree of activation of the oncogene may correspond to the number of oncogenes in the cell. Additionally or alternatively, the degree of activation of the oncogene may correspond to the expression levels of the oncogene in the cell. The degree of activation of the oncogene in the cell may result of one or more alterations in the cell. In examples, the alterations may include any one or any combination of: an increase of gene copy number, activating mutations, and/or inter or intra chromosomal rearrangements resulting in gene fusion.

The plurality of pieces of data provided at S10 each correspond to a given (i.e. respective/corresponding) cell of the tumor. One piece of data corresponds to one cell of the tumor. Each piece of data includes the degree of activation of the oncogene in its corresponding cell. In other words, each piece of data comprises a value representing the real degree of activation of the oncogene in the corresponding cell, possibly approximatively and/or by simulating such real degree of activation. In examples, the pieces of data may each include the degree of activation of more than one oncogenes associated with the tumor. The degree of activation of more than one oncogenes in a piece of data may be from different types of oncogenes. In examples, two pieces of data may comprise a degree of activation of different oncogenes.

The cells of the tumor corresponding to each piece of data of the plurality of pieces of data represent real tumor cells. In examples, the pieces of data provided at S10 may be determined with the available information on tumor cells of a person. The person may be a patient afflicted with cancer. In examples, each piece of data may be determined with information available on a respective single tumor cell. In such a case, the degree of activation of the oncogene in the cells included in the plurality of pieces of data provided at S20 may correspond to the real degree of activation of the oncogene in cells belonging to the tumor of the patient at a given point in time. Alternatively, the degree of activation of the oncogene in one or more pieces of data may be extrapolated from the available information on the tumor cells. In examples, the distribution of the degree of activation of the oncogene in the pieces of data of the plurality of pieces of data may correspond to the real distribution of the degree of activation of the oncogene in the population of cancer cells.

The information on proliferation outputted by the model provided at S20 may be any information representing the evolution in time of the cell (i.e. how the cell proliferates) and/or the evolution in time in the cell of mechanisms which can have an effect on the degree of activation of the oncogene in the cell. In examples the information on proliferation may include information on death or survival of the cell (i.e. information on if the cell has survived or not), on absence or presence of division (i.e. information on if the cell has divided, when it has survived), and/or on evolution of the degree of oncogene activation (i.e. information on if the degree of oncogene activation has changed relative to a parent cell, in the two cells resulting from the division of the parent cell, e.g. for example information on acquisition of one or more new alterations during the division).

The information on proliferation of the cell outputted by the model depends on the degree of oncogene activation in the cell. The dependence may be any relation which implements knowledge on real cellular processes. For example, it is known that the rate of division of the cell corresponding to the piece of data taken as input may increase if the degree of activation of the oncogene in the cell increases. In examples, the dependence may be such that as the degree of activation of the oncogene in a respective given cell inputted to the model increases, division of the respective given cell is more likely and/or increase of the degree of activation of the oncogene in the two cells resulting from a division of the relative to the degree of activation of the oncogene in the respective given cell is more likely (e.g. acquisition of one or more new alterations during the division is more likely). Thus, the model provides an accurate output.

The model is run S30 on one or more pieces of data of the plurality of pieces of data. The model simulates the evolution of one or more cells, each with a respective degree of activation of the oncogene associated with the tumor. The collective evolution of the cells simulates the evolution of the tumor. In examples, the simulation can be initiated from a single cell. Alternatively, the simulation can be initiated from a group of cells.

The plurality of pieces of data updated at S40 is representative of the evolution of the tumor. The updated pieces of data represent the cells corresponding to the plurality of pieces of data provided at S10 after the running in S30 at a later point in time. As such, the corresponding degree of activation of the oncogene included in the updated plurality of pieces of data corresponds to the degree of activation of the oncogene in the corresponding cell at said later point in time. At least one piece of data may remain unchanged after it is updated if the degree of activation of the oncogene in the cell represented by said at least one piece of data does not change after the simulation of the evolution of the cell. Alternatively or additionally, at least one piece of data may be modified after the simulation. In examples, at least one piece of data may be discarded if after the run S30 the information on proliferation of the cell corresponding to the piece of data includes information relative to cell death. A discarded piece of data may be deleted from the plurality of pieces of data during the updating S40. Alternatively or additionally, a new piece of data may be created for a cell resulting from the division of the cell corresponding to a piece of data taken as input during the running S30. In such a case, a value may be set. The plurality of pieces of data may be updated after each run of the model. Alternatively, the model may be run on multiple pieces of data before the plurality of pieces of data is updated with each respective information on proliferation of the cells.

The changes between the provided plurality of pieces of data and the updated plurality of pieces of data simulate the evolution of the tumor. Each updated piece of data has an updated degree of activation of the oncogene associated with the tumor, based on the simulation of the proliferation of the cell performed during the running S30. The simulated evolution of the tumor maintains a simulated heterogeneity reflected by the different degrees of activation of the oncogene in the different cells. Thus, the method allows to determine a prediction in the evolution in heterogeneity between the cells of the tumor.

In examples, each piece of data may further include a spatial localization of the cell corresponding to the respective piece of data. The spatial localization allows to locate the cell in a two-dimensional or three-dimensional space. The two-dimensional or three-dimensional space may have a maximum size. In other words, a maximum length according to a direction in the three-dimensional or two-dimensional space. In examples, the spatial localization may be a set of coordinates corresponding to a point, a surface or a volume. In examples, the spatial localizations may be specified with respect to a grid comprised of units (i.e. grid cells). In examples, the grid may be regular and/or the units may be cubic. The spatial localization of a cell may correspond to a respective unit. In examples, two cells may not be located at the same spatial localization. Such spatial localization allows the one or more updated pieces of data to provide additional information on the spatial distribution of the degree of activation of the oncogene when simulating the evolution of the tumor. Indeed, spatial intra-tumor heterogeneity relative to the degree of activation of the oncogene becomes apparent when positioning the cells corresponding to the updated plurality of pieces of data. In examples, the simulation of the evolution of a tumor may position in a three-dimensional or two-dimensional grid the updated plurality of cell and provide the user with the spatial intra-tumor heterogeneity of the simulated tumor.

In examples, the model provided at S20 may be further configured to determine if a cell undergoes division. The determination may depend on the degree of activation of the oncogene inside the cell. The information on proliferation of the cell when running (S30) the model may then include information respective to the presence or absence of division of the cell, depending on the determination performed by the model.

When the model determines that a respective cell divides, the information on proliferation of the respective cell outputted at S30 may allow the determination of the spatial localization of the two cells resulting from the division. Also, the information on proliferation may further allow the determination of the degree of activation of the oncogene in the two cells. In examples, the spatial localization of the two cells resulting from the division and their respective degree of activation of the oncogene may be included in the information on proliferation outputted at S30.

The spatial localization of the two cells resulting from the division may be in a neighborhood of the parent cell. The neighborhood of a given cell may be the space of all points at a distance below a predetermined threshold. The distance may be a Euclidian distance. The predetermined threshold may be strictly lower than a half of the maximum length of the two- or three-dimensional space. In examples, the predetermined threshold is lower than ten cell lengths and/or ten grid units. In examples, the predetermined threshold is equal to one cell length and/or one grid unit. In other words, the neighborhood may correspond to all spatial localizations adjacent to the given cell. For example, two spatial localizations at a distance equal to the length of a cell and/or two spatial localizations corresponding to two grid units which share a common face, edge or vertex. The spatial localization of one of the two cells resulting from division may correspond to the spatial localization of the cell corresponding to the piece of data taken as input by the model. In examples, if there is no cell division, the spatial localization of the cell does not change during the updating S40. Thus, the spatial localization of the cells resulting from division may depend on the spatial localization of the cell which underwent division. Therefore, updating the plurality of pieces of data maintains consistency of the initial distribution of spatial localizations of the cells. Consequently, the simulation may include a realistic spatial distribution of a next generation of cells with their respective degrees of activation of the oncogene.

In examples, the information on proliferation of the cell corresponding to a piece of data taken as input by the model may further depend on space availability in the neighborhood of the spatial localization of the cell. The space availability refers to whether a cell is located at a spatial localization or not. In other words, the space availability is dependent on if a spatial localization has been assigned to any cell or not.

In examples, the information relative to the presence or absence of division of a cell taken as input may be based on space availability in the neighborhood of the cell. In examples, for the model to positively determine during the run S30 that a cell corresponding to a piece of data taken as input undergoes division, at least one spatial localization, in the neighborhood of the spatial localization of the cell, must be an unoccupied spatial localization, thus not assigned to any cell. Each unoccupied respective spatial localization in the neighborhood of the spatial localization of the cell, is an available spatial localization which can be assigned to a cell resulting from division. In examples, the model may determine before the run S30 which spatial localizations are available from the available pieces of data. Alternatively, the model may perform the determination during the run, allowing multiple simulations to be run in parallel each corresponding to different pieces of data.

In examples, if the model determines during the run S30 that a cell corresponding to a piece of data taken as input divides, the information on proliferation of the cell may include for each cell resulting from the division, a respective degree of activation of the oncogene. The respective degree of activation of the oncogene is based on the degree of activation of the oncogene of the cell corresponding to the piece of data taken as input by the model. The degree of activation of the oncogene of the cells resulting from the division may be different from each other and may also be different from the degree of oncogene activation of the cell corresponding to the piece of data taken as input. Indeed, during the run S30, the degree of activation of the oncogene may vary due to simulated alterations occurring in the cell. This allows the model to more closely simulate the evolution of the tumor. In examples, the model may take into account new alterations such as new mutations and/or asymmetric cell division. The new mutations and/or asymmetric cell divisions may increase in frequency if the initial degree of activation of the oncogene increases. Alternatively or additionally, the degree of oncogene activation of the cells resulting from division may be the same as the cell corresponding to the piece of data taken as input by the model. Thus the accuracy of the simulation of the evolution of the tumor may be improved. Indeed, the method may simulate tumors where new alterations do not appear systematically in tumor cells.

In examples, the degree of oncogene activation of each cell resulting from the division may correspond to an at least partly probabilistic variation of the degree of oncogene activation in the respective given cell. By "at least partly probabilistic", it is meant that the variation depends on a random variable. Additionally, the variation may further depend on a deterministic variable. In examples, the variation of the degree of oncogene activation in the respective given cell may depend on a random variable and a fixed value, for example on a comparison of a generated value of the random variable with the fixed value. The random variable may be a number between 0 and 1 generated according to a uniform probability distribution on range [0,1], and the fixed value may represent the probability of the occurrence of a biological process. A generated value of the random variable may then be compared to the fixed value, thereby emulating over iterations of the running S30 the probability. Thus, the model provided at S20 may take into account the probabilistic nature of the biological processes governing the evolution of cells.

For example, the degree of activation of the oncogene in the cell may increase based on the probability for an alteration to appear. In examples, the probability of occurrence of one or more biological processes of the cell may be determined based on a threshold value determined from mathematical models. Additionally, the computations performed by the model during S20 which relate to the changing of the degree of activation of the oncogene in the cell may be performed only when the model determines that the cell undergoes division. Thus, the model uses less computation resources during each run S30 while staying true to biological considerations. Indeed, alterations may appear mostly during cell division. Additionally or alternatively, the degree of oncogene activation in the cells resulting from division may be based on asymmetry of the cell division which also follows probabilistic rules. As such, the simulated evolution of the tumor is based on the degree of oncogene activation of the cells and subject to probabilistic variations inherent to the mechanisms which govern the evolution of cells, increasing the accuracy of the simulation.

In examples, the model provided at S20 may be a decision-based model, for example a decision tree model. A decision-based model performs a simulation by presenting decisions which lead to at least two possible outcomes, depending on parameters of the model. In examples, the model may be such that once an outcome is determined, a new decision may be presented again. The new decision also leads to at least two outcomes. The model provided at S20 may include a decision on the death or survival of the cell corresponding to the piece of data taken as input. Then, if the outcome is that the cell survives, a decision on the absence or presence of cell division may follow. Then, if the outcome is that the cell divides, a decision on acquisition of new alterations may follow, for example which may change the degree of activation of the oncogene in the cell. The new alterations may be related to the acquisition of a new centromere, the acquisition of new mutations, alteration of the chromosome, gain or loss of chromosomal copy number and/or asymmetric division. The decisions may be influenced by the degree of activation of the oncogene in the cell corresponding to the piece of data taken as input. Alternatively, the decisions may be influenced by the degree of activation of the oncogene in the cell when the decision is taken. A decision-based model allows to follow the different stages in the evolution of a tumor cell in the order they appear. Thus, the degree of activation of the oncogene in the resulting cells is a consequence of an order simulation of biological processes. Consequently, the accuracy of the simulation of the evolution of the tumor increases.

Additionally, each decision may be determined based on the outcome of a computation relative to a probability. The probability may depend on the degree of activation of the oncogene in the cell. As such, the model provided at S20 simulates both a sequence of events that may lead to a change in the degree of activation of the oncogene inside a cell and the probabilistic nature of biological mechanisms. Thus, the accuracy of the simulation of the evolution of a tumor is further increased.

In examples, a treatment type may be provided and the information on proliferation may further depend on the treatment type. The treatment type may involve one or more treatments or a combination of treatments, such as drug treatments or therapeutic treatments. The model provided at S20 may then be further configured to take into account the treatment type when determining if a cell corresponding to a piece of data taken as input survives. Determining if a cell corresponding to a piece of data taken as input survives may be performed at any point during the run. The simulation of the evolution of the tumor may thus predict a relative efficacy for a specific treatment or a combination of treatments. In examples, the treatment type may be selective, such as a treatment targeted at one or more specific oncogenes. Alternatively or additionally, the treatment type may be general, such as chemotherapy. As such, the accuracy of the prediction of the relative efficacy for a treatment or a combination of treatments may be increased by taking into account the mechanism of action of the one or more treatments.

In examples, after updating S40 the plurality of pieces of data with the results of the running, an iteration S50 may be performed by running the model again taking as input one or more pieces of data from the updated plurality of pieces of data. The updated plurality of pieces of data may comprise new pieces of data that resulted from the division of cells in a previous run of the model. For each iteration, after running S30 the model with one or more pieces of data from the updated plurality of pieces of data, the updated plurality of pieces of data is further updated based on the results of the new run(s). This allows to simulate the evolution of the tumor over time by simulating several generations of cells. Consequently, the simulation of the evolution of the tumor may be performed to estimate the tumor after a given amount of time has passed. In examples, a time leap may be associated to a cell corresponding to a piece of data each time the piece of data is taken as an input of the model.

In examples, after updating, the plurality of cells corresponding to the plurality of pieces of data are considered as having advanced in time for a duration equal to the time needed to complete a cell cycle.

In examples, after updating, the plurality of pieces of data are considered as having advanced in time for a duration equal to:

$$\frac{n}{N}(\text{time needed to complete a cell cycle})$$

Where n is the number of pieces of data taken as input and N is the number of pieces of data in the plurality of pieces of data. For example, if one tenth of the pieces of data are taken as input, the population of cells advances in time, after the updating, by a one tenth of the time needed to complete a cell cycle. This allows an asynchronous simulation of the cells of the tumor.

In examples, prior to providing the model at S20, data relative to the patient having the tumor may be provided. The model provided at S20 may then be adjusted based on the data relative to the patient. By "adjusted", it is meant that at least one parameter of the model may be modified depending on the data relative to the patient. If a value for a parameter of the model was null, a value may be set. For example, the probability of cell mutation may depend on way of life data or other clinical data of the patient. Way of life data may comprise any one or a combination of smoking, Body mass index (BMI) and/or age. The data relative to the patient may include physical data. The physical data may comprise any one or a combination of height, weight, body mass index (BMI) or any information related to the way of life of the patient. Alternatively or additionally, the data relative to the patient may include medical information of the patient, The medical information of the patient may include any one or a combination of genetic risk factors, medical history, way of life of the patient or any information related to genetic diseases of the patient. Additionally or alternatively, the model may be adjusted through a calibration on a specific cohort of patients. In examples, the specificity may be the tumor location or the oncogenes.

By adjusting the model provided at S20 with the data relative to the patient, the simulation of the evolution of the tumor becomes personalized to said patient. This increases the accuracy of the simulated evolution of the tumor of said patient. Alternatively, the model provided at S20 may be configured from data from the literature. For example, when data relative to the patient is unavailable.

Figure 2:
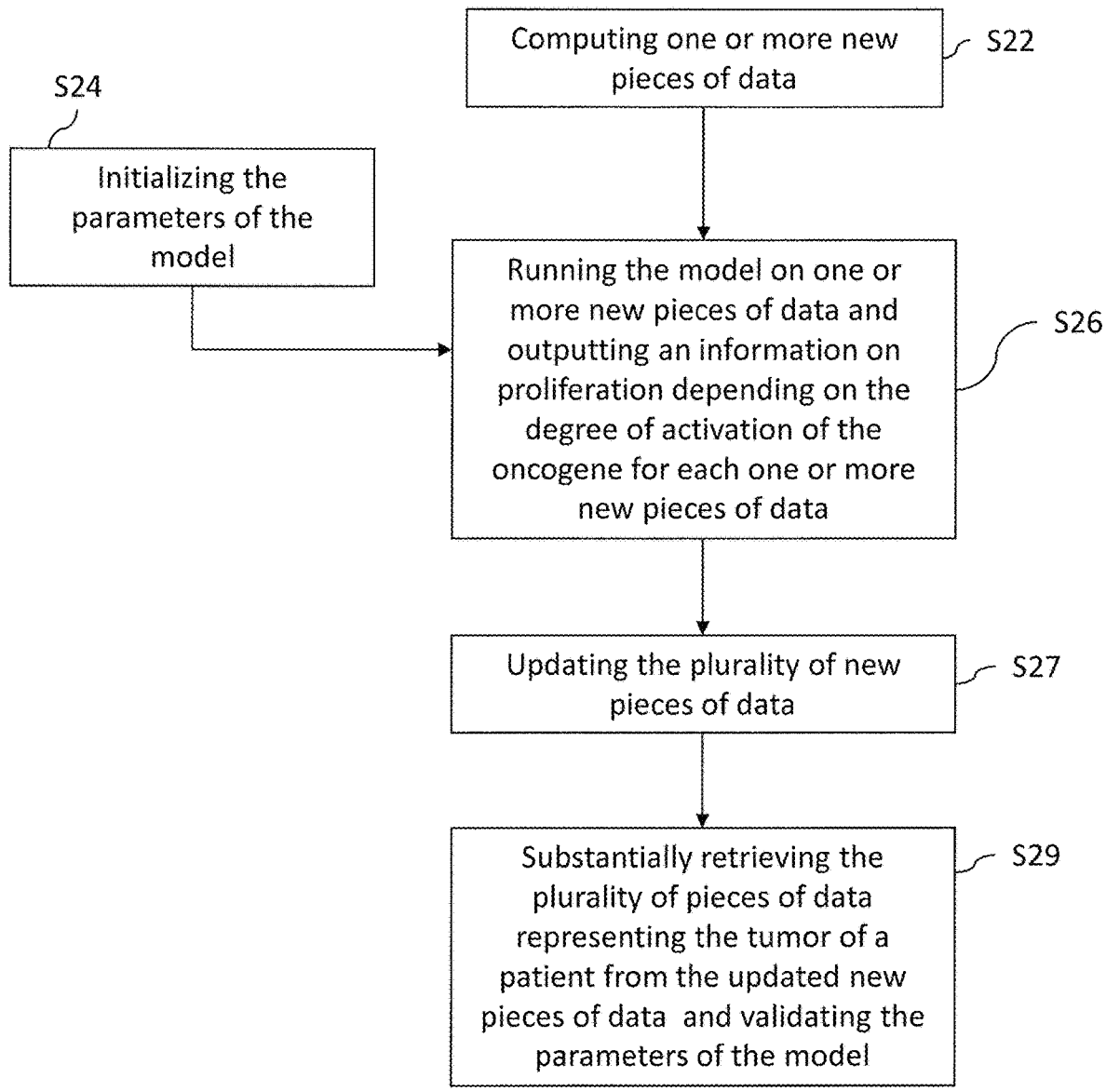
FIG. 2 shows a flowchart of an example of adjusting the parameters of the model with data relative to the patient.

Now referring to FIG. 2, in examples the model provided at S20 may comprise one or more parameters. The parameters may be determined by configuring values so that it is possible to retrieve the plurality of pieces of data provided at S10. The retrieval may be performed by defining one or more other pieces of data S22. Each other piece of data may correspond to a given cell of an initial state of the tumor and include a degree of activation of an oncogene associated to the tumor in the given cell. The initial state of the tumor may be comprised of one or more cells which may lead to a tumor, such as the tumor represented by the plurality of pieces of data provided at S10. One or more other pieces of data may correspond to a selected part of the plurality of pieces of data provided at S10. Alternatively or additionally, one or more other pieces of data may each be assigned a random spatial localization and a random degree of activation of the oncogene.

The parameters of the model are initialized S24. In other words, first values for the parameters of the model are chosen.

Next, the model is run S26 on one or more other pieces of data defined at S22.

Next, the one or more other pieces of data are updated S27 based on the result of the running S26.

Next, S26 and S27 may be iterated so as to increase the number of other pieces of data forming a plurality of other pieces of data and simulate the advancement of the tumor in time.

Next the updated plurality of other pieces of data is compared to the pieces of data of the plurality of pieces of data provided at S10.

If the cells corresponding to the pieces of data of the updated plurality of other pieces of data are substantially the same as the cells corresponding to the pieces of data of the plurality of pieces of data provided at S10, the values of the parameters are validated S29. "Substantially the same" means that the cells corresponding to the other pieces of data of the updated plurality of other pieces of data and the cells corresponding to the pieces of data of the plurality of pieces of data provided at S10 have values which are similar, within a tolerance margin which may be defined automatically or by user input. The similar values between the cells may comprise the respective degree of activation of the oncogene in the cells and/or the respective spatial localization of the cells. Alternatively, the comparison may relate to the distribution of the degree of oncogene activation between the population of cells.

If the cells corresponding to the other pieces of data of the updated plurality of other pieces of data are not substantially the same as the cells corresponding to the pieces of data of the plurality of pieces of data provided at S10, the values of the parameters of the model are changed according to the similarities between the compared cells and the process is repeated. Additionally or alternatively, several iterations of running and updating may be performed on the other pieces of data prior to the comparison with the plurality of pieces of data provided at S10. In examples, iterations are executed until the number of other pieces of data of the updated plurality of other pieces of data is substantially the same as the number of pieces of data of the plurality of pieces of data provided at S10. Alternatively, iterations may be performed so that the distribution of the degree of activation of the oncogene in the cell population of the updated plurality of other pieces of data is substantially the same as the distribution of the degree of activation of the oncogene in the cells corresponding to the provided pieces of data at S10. The comparison between the cells corresponding to the other pieces of data of the updated plurality of the other pieces of data and the cells corresponding to the pieces of data of the plurality of pieces of data provided at S10 may be performed between each iteration. Alternatively, the comparison may be performed after a number of iterations.

By adjusting the parameters of the model using as a comparison reference the plurality of pieces of data provided at S10, the accuracy of the simulation of the evolution of the tumor performed with such a model is further increased. Indeed, the cells corresponding to the pieces of data of the plurality of pieces of data provided at S10 represent real tumor cells. Therefore, retrieving real world data from simulations on a sample of the tumor indicates that the parameters of the model are properly adjusted and will be more accurate to reality. Therefore, the simulation of the evolution of the tumor whose cells correspond to the pieces of data of the plurality of pieces of data provided at S10 will be accurate.

In examples, the first values of the parameters of the model during the initialization S24 are based on the data relative to the patient. In other words, the data relative to the patient may be used as prior data for the parameters of the model. This increases the accuracy of the model for a given patient and avoids combinations of parameters which may not correspond to the patient. Indeed, The model comprises more than one parameter, as such there may be more than one combination of values for the parameters which may lead to similar simulations. Depending on the initial values chosen during the initialization of the parameters at S24, different combinations for the values of the parameters may be reached when adjusting the model. By initializing the parameters based on data relative to the patient, the parameter values validated at S29 are directly related to the data of the patient. This further personalizes the simulation of the evolution of the tumor. Thus, the accuracy of the simulation is increased.

Figure 3:
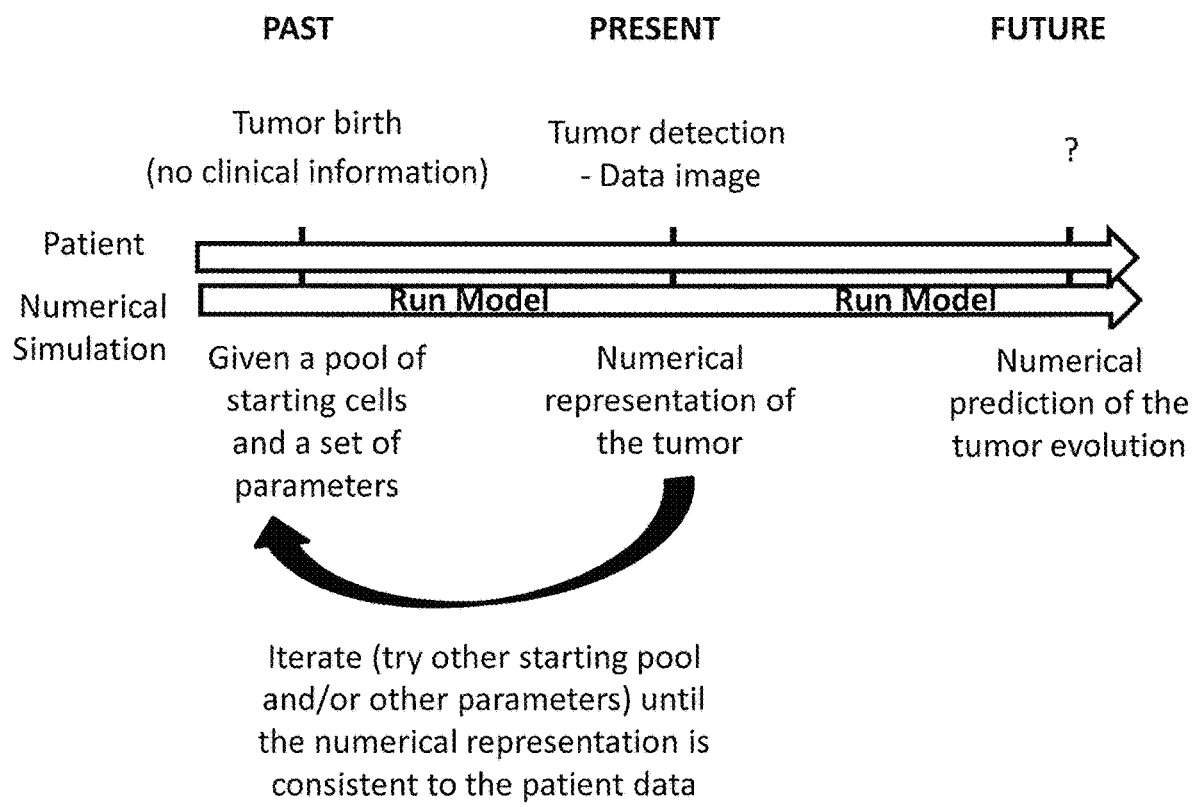
FIG. 3 shows a diagram of an example of the method comprising calibrating the model.

Referring now to FIG. 3, an example of the process of simulating the evolution of a tumor with the calibration of the model is shown. The PAST data from the patient's tumor is unknown as there is no clinical information on when it was first developed. For the sake of calibrating the model provided a pool of cells and a set of parameters is selected and/or computed. The PRESENT data from the patient's tumor comprises an image of the tumor from which a numerical representation of the current tumor may be computed, for example in the form of pieces of data. The model is run with the pool of cells and the parameters of the PAST data until it is substantially the same as the numerical representation computed from the PRESENT data. Then, the model is calibrated and may be used to perform numerical predictions of the evolution of the tumor which are representative of the FUTURE data.

Back to FIG. 1, in examples after the plurality of pieces of data are updated S40 at least once, statistics relative to the oncogene and based on the plurality of pieces of data may be computed. The statistics may comprise computing the shape and values of the distribution of the degree of activation of the oncogene in the cell population corresponding to the updated plurality of pieces of data. Additionally, the statistics may further comprise a spatial distribution of the degree of activation of the oncogene in the cells corresponding to the pieces of data of the updated plurality of pieces of data. From the statistics a spatial representation indicating zones with different degrees of activation of the oncogene of the tumor may be further computed. From the spatial representation or the computed statistics, the user may retrieve the predicted intra-tumor spatial-heterogeneity. In addition, the statistics may comprise computing a numerical value of the heterogeneity and presenting it to the user along with a tumor size.

The method for simulating the evolution of a tumor may be used to assist medical experts in selecting the treatment most suited to a patient. Indeed, the simulation of the evolution of the tumor may predict the growth of the tumor, allowing a medical expert to adjust treatment priority on patients. Additionally or alternatively, the method may further assist the medical expert in selecting a treatment selection, given that the simulation may predict the intra-tumor heterogeneity. In addition, the method is adapted to the time constraints of medical professionals. Indeed, the simulation may focus on a limited number of oncogenes without performing computations corresponding to large portions of the genome of the cell. This allows the simulations to be substantially short, so as to be used in clinics or hospitals for patients which cannot stay for extended periods of time.

The method is computer-implemented. This means that steps (or substantially all the steps) of the method are executed by at least one computer, or any system alike. Thus, steps of the method are performed by the computer, possibly fully automatically, or, semi-automatically. In examples, the triggering of at least some of the steps of the method may be performed through user-computer interaction. The level of user-computer interaction required may depend on the level of automatism foreseen and put in balance with the need to implement user's wishes. In examples, this level may be user-defined and/or pre-defined.

A typical example of computer-implementation of a method is to perform the method with a system adapted for this purpose. The system may comprise a processor coupled to a memory and a graphical user interface (GUI), the memory having recorded thereon a computer program comprising instructions for performing the method. The memory may also store a database. The memory is any hardware adapted for such storage, possibly comprising several physical distinct parts (e.g. one for the program, and possibly one for the database).

Figure 10:
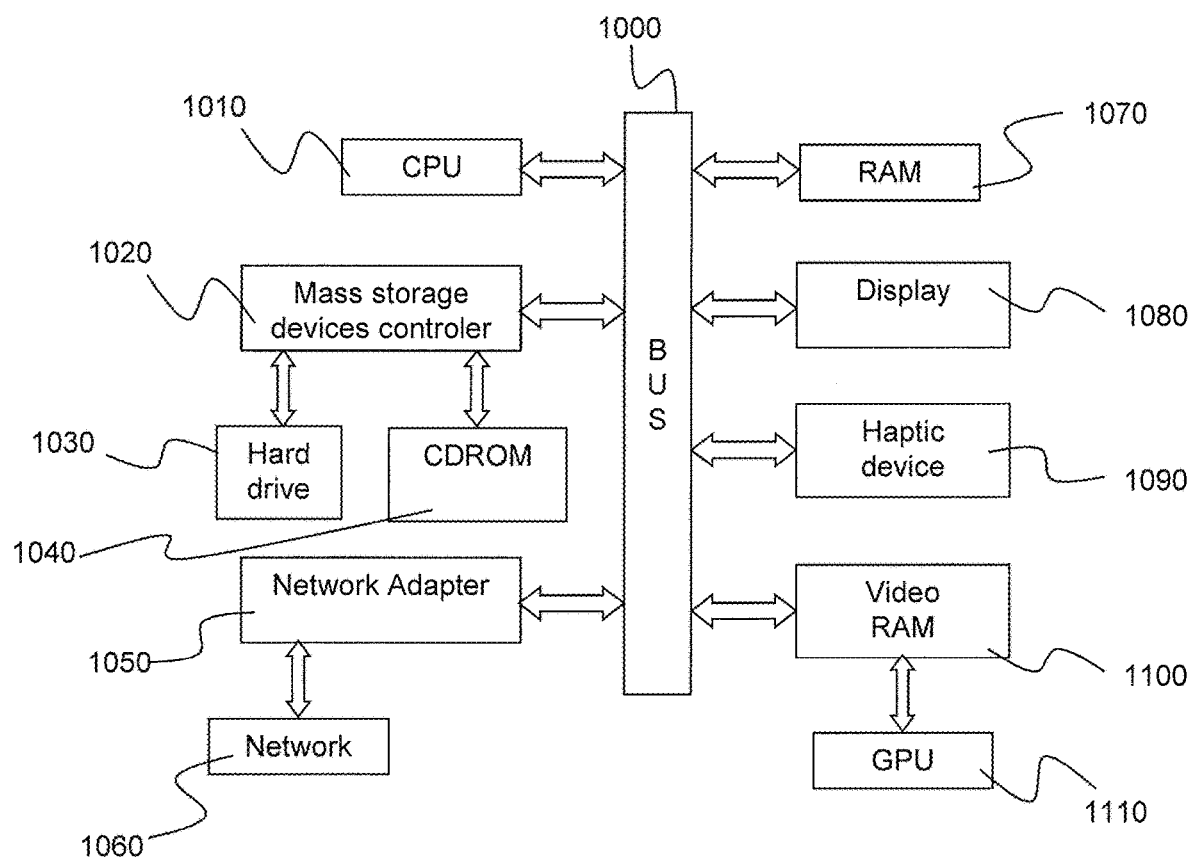
FIG. 10 shows an example of the system.

FIG. 10 shows an example of the system, wherein the system is a client computer system, e.g. a workstation of a user.

The client computer of the example comprises a central processing unit (CPU) 1010 connected to an internal communication BUS 1000, a random access memory (RAM) 1070 also connected to the BUS. The client computer is further provided with a graphical processing unit (GPU) 1110 which is associated with a video random access memory 1100 connected to the BUS. Video RAM 1100 is also known in the art as frame buffer. A mass storage device controller 1020 manages accesses to a mass memory device, such as hard drive 1030. Mass memory devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks 1040. Any of the foregoing may be supplemented by, or incorporated in, specially designed ASICs (application-specific integrated circuits). A network adapter 1050 manages accesses to a network 1060. The client computer may also include a haptic device 1090 such as cursor control device, a keyboard or the like. A cursor control device is used in the client computer to permit the user to selectively position a cursor at any desired location on display 1080. In addition, the cursor control device allows the user to select various commands, and input control signals. The cursor control device includes a number of signal generation devices for input control signals to system. Typically, a cursor control device may be a mouse, the button of the mouse being used to generate the signals. Alternatively or additionally, the client computer system may comprise a sensitive pad, and/or a sensitive screen.

The computer program may comprise instructions executable by a computer, the instructions comprising means for causing the above system to perform the method. The program may be recordable on any data storage medium, including the memory of the system. The program may for example be implemented in digital electronic circuitry, or in computer hardware, firmware, software, or in combinations of them. The program may be implemented as an apparatus, for example a product tangibly embodied in a machine-readable storage device for execution by a programmable processor. Method steps may be performed by a programmable processor executing a program of instructions to perform functions of the method by operating on input data and generating output. The processor may thus be programmable and coupled to receive data and instructions from, and to transmit data and instructions to, a data storage system, at least one input device, and at least one output device. The application program may be implemented in a high-level procedural or object-oriented programming language, or in assembly or machine language if desired. In any case, the language may be a compiled or interpreted language. The program may be a full installation program or an update program. Application of the program on the system results in any case in instructions for performing the method.

The following is a discussion on treatment decisions relating to tumors upon which the method builds.

The discussion refers to the following list of academic literature documents:

1. Ammari S, Thiam R, Cuenod C A, et al. Radiological evaluation of response to treatment: application to metastatic renal cancers receiving anti-angiogenic treatment. Diagn Interv Imaging. 2014 June; 95(6):527-39.
2. Cardoso F, et al. 3rd ESO-ESMO International Consensus Guidelines for Advanced Breast Cancer (ABC 3). Ann Oncol. 2017 Feb. 19. doi: 10.1093/annonc/mdx036.
3. Lindeman N I, et al. Molecular testing guideline for selection of lung cancer patients for EGFR and ALK tyrosine kinase inhibitors: guideline from the College of American Pathologists, International Association for the Study of Lung Cancer, and Association for Molecular Pathology. J Mol Diagn. 2013; 15(4):415-53.
4. Novello S., et al. Metastatic non-small-cell lung cancer: ESMO Clinical Practice Guidelines for diagnosis, treatment and follow-up. Ann Oncol. 2016 September; 27(suppl 5):v1-v27asymptotic analysis." Computational & Applied Mathematics (2006).
5. Watanabe T. Model Systems Facilitating an Understanding of Mechanisms for Oncogene Amplification. Oncogene and Cancer—From Bench to Clinic, book edited by Yahwardiah Siregar, ISBN 978-953-51-0858-0, Published: Jan. 24, 2013.
6. Wolff A C, et al. Recommendations for Human Epidermal Growth Factor Receptor 2. J Clin Oncol; 2013.
7. Anderson A R A, Weaver A M, Cummings P T, Quaranta V. Tumor morphology and phenotypic evolution driven by selective pressure from the microenvironment. Cell. 2006; 127(5):905-915inpainting." IEEE Transactions on Image Processing 2004.
8. Buckley, N E et al. Quantification of HER2 heterogeneity in breast cancer—implications for identification of subdominant clones for personalised treatment. Sci Rep. 2016; 6: 23383.
9. Cottu P H, et al. Intratumoral heterogeneity of HER2/neu expression and its consequences for the management of advanced breast cancer. Ann Oncol 2008; 19: 595-7.
10. Dowsett M et al. Disease-free survival according to degree of HER2 amplification for patients treated with adjuvant chemotherapy with or without 1 year of trastuzumab: the HERA Trial. J Clin Oncol 2009; 27(18): 2962-9.
11. Iwasaki W M, et al. Simulation framework for generating intratumor heterogeneity patterns in a cancer cell population. PLoS One. 2017; 12(9): e0184229.
12. Lee H J, et al. HER2 Heterogeneity Affects Trastuzumab Responses and Survival in Patients With HER2-Positive Metastatic Breast Cancer. Am J Clin Pathol 2014; 142: 755-766.
13. Lefebvre, G., Cornelis, F., Cumsille, P., Colin, T., Poignard, C., & Saut, O. (2016). Spatial modelling of tumour drug resistance: the case of GIST liver metastases. Mathematical medicine and biology: a journal of the IMA, 34(2), 151-176.

14. Nitta H, et al. The assessment of HER2 status in breast cancer: the past, the present, and the future. Pathol Int. 2016; 66(6):313-24.
15. Poleszczuk J, Hahnfeldt P, Enderling H. Evolution and phenotypic selection of cancer stem cells. PLoS Comput. Biol. 2015; 11(3):e1004025.
16. Ribba, B., Colin, T., Schnell, S., 2006. A multiscale mathematical model of cancer, and its use in analyzing irradiation therapies. Theoretical Biology and Medical Modelling 3,1.
17. Starczynski J et al. HER2 Gene Amplification in Breast Cancer: A Rogues' Gallery of Challenging Diagnostic Cases: UKNEQAS Interpretation Guidelines and Research Recommendations. Am J Clin Pathol 2012; 137:595-605.
18. Sottoriva A, Kang H, Ma Z, Graham T A, Salomon M P, Zhao J, et al. A Big Bang model of human colorectal tumor growth. Nat. Genet. 2015; 47(3):209-216
19. Yap T A, et al. Sci Transl Med. Intratumor heterogeneity: seeing the wood for the trees. 2012; 4(127):127ps10.
20. Ferrari A, et al. A whole-genome sequence and transcriptome perspective on HER2-positive breast cancers. Nat Commun. 2016; 7:12222.
21. Marotta M, Chen X, Inoshita A, Stephens R, Thomas Budd G, Crowe J P, et al. A common copy-number breakpoint of ERBB2 amplification in breast cancer colocalizes with a complex block of segmental duplications. Breast Cancer Research 2012; 14, R150. doi:10.1186/bcr3362.
22. Marotta M. Palindromic amplification of the ERBB2 oncogene in primary HER2-positive breast tumors. Sci Rep. 2017; 7:41921.
23. NICE guideline, accessed 2017 Jun. 21. https://pathways.nice.org.uk/pathways/advanced-breast-cancer #path=view %3A/pathways/advanced-breast-cancer/managing-advanced-breast-cancer.xml&content=view-node %3Anodeshrpos-and-her2pos.
24. NCCN guidelines, accessed 2017 Jun. 21. https://www.nccn.org/professionals/physician_gls/pdf/breast.pdf
25. Barnard M E, et al. Established breast cancer risk factors and risk of intrinsic tumor subtypes. Biochim Biophys Acta. 2015; 1856(1):73-85.
26. O'Brien K M, et al. Breast cancer subtypes and previously established genetic risk factors: A Bayesian approach. Cancer Epidemiol Biomarkers Prev. 2014 January; 23(1): 84-97.

In medicine, treatment decisions are based on diagnosis. For example, an oncologist may treat invasive breast cancer after diagnosed on a tumor biopsy and staged from extended radiological or pathological examinations. In precision medicine, biological markers (biomarkers) may be added to support clinical decisions, as they help refine a diagnosis and assist in predicting treatment outcome. For example, breast cancers are divided in different subgroups based on the expression of oestrogen receptors, progesterone receptors and HER2 (Human Epidermal Receptor 2), and they guide use of hormone therapy and anti-HER2 targeted therapies. Companion diagnostic test is a biomarker specifically designed to be paired with a specific drug. Companion diagnostics are medical devices that may help doctors decide which treatments to offer patients and which dosage to give, tailored specifically to the patient. Currently, 39 companion tests based on genetic or histologic biomarkers are approved by the Federal Drug Agency.

One major limitation for biomarkers (and companion diagnostic test) results interpretation is the inter-individual variability, as observed for many biological processes, meaning that values are distributed with respect to a statistical distribution. Another limitation of biomarkers usability is intra-tumor heterogeneity, a common phenomenon in which different cancer cell populations may co-exist in a single tumor. In such a situation it is unclear which cell populations the companion tests should target.

The current biomarkers do take into account of the inter-individual and intra-tumor heterogeneity, even when the genetic intra-tumor heterogeneity is assessed by an approved test, such as In Situ Hybridization (ISH) and/or protein expression by Immuno-Histo-Chemistry (IHC) used to detect HER2 gene amplification, ALK gene fusion, RET gene fusion, ROS1 gene fusion, CD274 (PD-L1) expression, ESR/PGR (Hormone Receptor) expression.

Currently, these biomarkers are based on the discretization of a quantitative measure using a unique cutoff point to identify eligible patients for a specific treatment. The cutoff point for gene amplification or protein expression results from expert guidelines. Examples of cutoff points include:

HER2 expression (IHC) in more than 10% of cells [6]
HER2 gene amplification (ISH) in more than 10% of cells, defined by average HER2 copy number≥6.0 signals/cell or ratio HER2/centromere ratio≥2.0 [6]
ALK gene fusion in more than 15% of cells [3]

Currently, all patients with a positive biomarker are eligible for FDA-approved drugs. For example, HER2-positive breast cancer patients are all preferably treated with a combination of pertuzumab-trastuzumab plus chemotherapy in first-line, and with ado-trastuzumab emtansine (TDM-1) in second-line [2], whatever the HER2 pattern. In the example of lung cancer, ALK-positive lung cancer patients are all eligible to ALK-inhibitors at first-line treatment [4].

Although guidelines recommend a clear cutoff point for interpretation, borderlines cases or unusual patterns of the biomarkers are frequent. Many studies have reported that about 10% of breast cancers have HER2 gene amplification heterogeneity [8,9,17], a situation associated with worse survival when treated with trastuzumab, a therapeutic anti-HER2 monoclonal antibody [12].

Inter-patient variability may also be taken into account for precision therapy. Indeed, Dowsett et al. showed that HER2 amplification level follows a gaussian distribution in a large patient population and suggested a negative correlation of HER2 amplification level with trastuzumab efficacy.

Cancer is a dynamic process. Treatment decisions in oncology are based on the effect of a treatment and on its evolution. One of the means for evaluating the dynamic evolution of a tumor under treatment is comparing tumor size on medical imaging before and after treatment using RECIST evaluation criteria. However, RECIST does not take into account the genetic tumor heterogeneity. By contrast, dynamic evaluation of genetic tumor heterogeneity biomarkers is not feasible in clinics because patient follow-up by multiple biopsies is not compliant with clinical constraints, the need of rapid treatment decisions, treatment initiation and ethics.

The proposed method for the simulation of the evolution of a tumor takes into account heterogeneous cell populations and improves patient selection without using cut-off points or systematic rules such as only taking into account the major population.

The method for simulating the evolution of a tumor can be used to empower the therapeutic decision. For example, when a genetic and/or histologic biomarker is required to predict the anti-tumor efficacy of different treatments or combinations of treatments. The method for simulating the evolution of a tumor may simulate the evolution of oncogenes and their spatial intra-tumor heterogeneity during tumor growth and during cancer treatments. In the example of breast cancer cells, the oncogenes inside said cells may be activated by different alterations, such as the increase of gene copy number, also called amplifications (i.e. HER2 amplification), activating mutations (such as KRAS p.G12C, or EGFR p.L858R), or inter or intra chromosomal rearrangements resulting in gene fusion (i.e., ALK gene fusion).

The method may improve predictions relating to the tumor growth and treatment efficacy depending of the intra-tumor heterogeneity of oncogenes.

An implementation of the method is now discussed.

In this implementation, a plurality of pieces of data each corresponding to a cell of the tumor of a patient are provided. Each piece of data including a degree of activation of one or more oncogenes associated to the tumor and a spatial localization assigned to the cell. The degree of activation of each oncogene may be a numerical value corresponding to the number of oncogenes in the cell. The plurality of pieces of data may be determined from an image of the tumor cells of the patient. It is further provided a model configured to take an input piece of data and to output an information on the proliferation of the respective cell corresponding to the input piece of data.

The information on proliferation includes information on death or survival of the cell, and/or information on the presence or absence of division of the cell, and/or information on the acquisition of one or more new alterations during a division. The information on the acquisition of one or more new alterations may include information on the acquisition of any one or a combination of a centromere, breakage-fusion-bridge extension event and/or unbalanced chromosome segregation.

The information on proliferation depends on the degree of activation of the one or more oncogenes in the cell. Notably, the information on proliferation is more likely to be indicative of presence of division as the degree of activation increases. Also, the information on proliferation is more likely to be indicative of acquisition of one or more new alterations as the degree of activation increases.

Further, the information on proliferation is indicative of presence of division depending on the space availability in a neighborhood of the cell. Notably, the information on proliferation can be indicative of presence of division only if space availability exists in the neighborhood of the cell.

When the information on proliferation includes information on the presence of division, a respective spatial localization for each cell resulting form the division is also included in the information on proliferation. The information on the respective spatial localization of each cell resulting from division allows to assign a spatial localization to each cell resulting from division. The spatial localization of each cell resulting from a single division may be in the neighborhood of one another. The spatial localization of one of the cells resulting from the division is located at the spatial localization of the cell corresponding to the piece of data taken as input.

When the information on proliferation includes information relative to the presence of division, the information on proliferation further includes a respective degree of activation of the one or more oncogenes in each cell resulting from the division. The degree of activation of the one or more oncogenes in each cell resulting from the division depends on the degree of activation of the one or more oncogenes of the cell corresponding to the piece of data taken as input.

The model is run on one or more pieces of data. The plurality of pieces of data updated based on the result of the run(s). The updating is performed based on information on proliferation of a cell corresponding to a piece of data taken as input. Therefore, the updating is cell-wise, as information on individual cells is used to update the plurality of pieces of data.

When updating, one or more pieces of data are created when the information on proliferation includes the presence of division. Thanks to the spatial localization included in the pieces of data before and after the run, the cells corresponding to the plurality of pieces of data are spatially coordinated. Therefore, the arrangement in space of the cells corresponding to the plurality of pieces of data follows the constraints of cell division.

When updating, at least one piece of data is discarded when the information on proliferation of the cell corresponding to said at least one piece of data includes information relative to cell death.

When updating, the degree of activation of one or more oncogenes included in at least one piece of data is unchanged when the information on proliferation of the cell corresponding to said at least one piece of data includes information on the absence of division or at least does not include information on the presence of division.

When updating, when the information on proliferation of at least one cell corresponding to a piece of data taken as input includes the acquisition of at least one alteration, the degree of activation of one or more oncogenes in at least one cell resulting from division increases.

After updating the plurality of pieces of data, one or more iterations are repeated. The iterations comprise running the model on one or more pieces of data of the updated pieces of data and updating the updated pieces of data based on the results of the running. Any cell corresponding to a piece of data taken as input corresponds to the cell at a later point in time. Therefore, through several iterations the model simulated the evolution of a tumor. Thanks to the pieces of data corresponding to individual cells of the tumor, the accuracy of the simulation of the evolution of a tumor is increased. The data injected into the model at each run is relatively small (i.e. consisting of only a degree of activation of the one or more oncogenes and a spatial localization).

Optionally, a treatment type is further provided. The treatment type includes any one or a combination of targeted treatments and/or general treatments. Targeted treatments are more effective on cells having one or more specific oncogenes. In such cases, the information on proliferation depends on the treatment type. The information on proliferation is more likely to include information on cell death when a treatment type effective on the cells corresponding to the plurality of pieces of data is provided. By taking into account the treatment type, the simulation of the evolution of a tumor predicts the efficacy of the treatment type with respect to the tumor. Different treatment types can be provided. The simulation on the evolution of a tumor can provide a comparison on the efficacy for each treatment type.

The model comprises parameters which are fixed. Optionally, patient data is provided, and the parameters of the model are adjusted from patient data. The patient data is from the same patient as the data from which the plurality of pieces of data are determined. Adjusting the parameters is performed by changing one or more values of the parameters. The patient data is information relative to the patient. The patient data comprises physical information and/or medical information. By adjusting the parameters from patient data, the simulation of the evolution of a tumor takes into account additional data specific to the patient. Thus, the simulation of the evolution of a tumor is personalized to the patient and its accuracy increases.

The following is an example of such an implementation of the method, referring to FIGS. 3-8 and to the previously provided list of academic literature documents.

Tumor heterogeneity evolution through time can catch inter-individual and intra-tumor heterogeneity and thus may help predict the best treatment strategy, including combinations of treatments. By contrast, current biomarker development has focused on selecting the "best" cutoff point to select the patient population that will benefit for a specific treatment.

Furthermore, the presented method is based on a biology-driven specific model for oncogene amplification.

The method may predict tumor evolution by means of a single time-point analysis, which improves on RECIST evolution measurements.

The model may be coded in any programming language including but not limited to python and OpenGL. The method deals with personalized medicine, may take into account genomics, patient as well as tumor properties (such as type and/or location) and patient characteristics.

Figure 4:
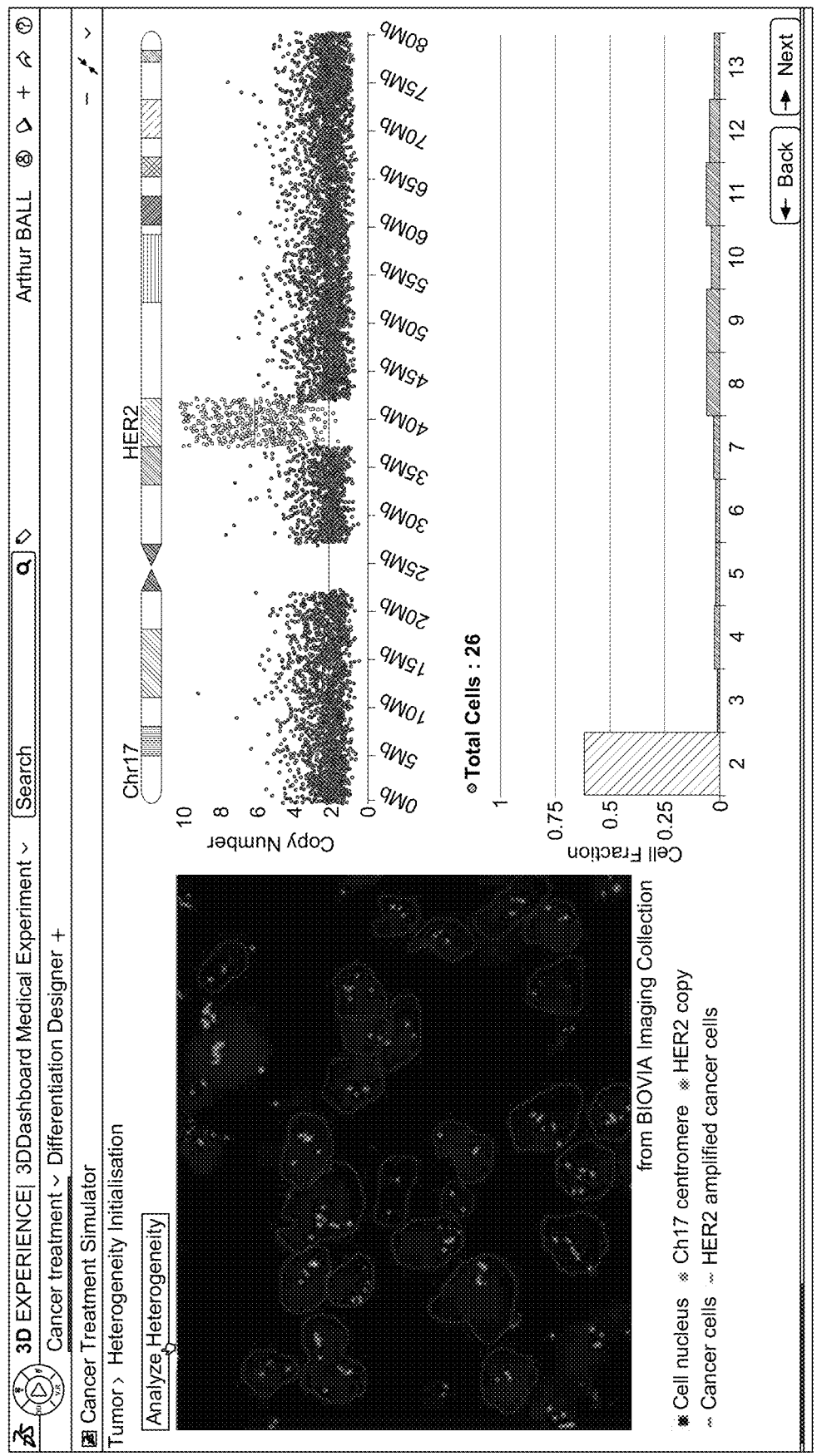
FIG. 4 shows an example of an image of analyzed tumor cells for building the plurality of pieces of data.

Referring to FIG. 4, a plurality of pieces of data may be computed from single cells data comprising information for oncogene activation. Single cell data for oncogene activation (i.e. HER2 amplification) may be obtained by means of FISH image analyses, by counting the number of HER2 and CEP17 signals. Other types of images of tumor cells may also be used to extract the tumor cell data. FIG. 4 shows a FISH analysis published by Starczynski J et al. The FISH image may be treated to delineate each nucleus, quantifying CEP17 and HER2 signals in each cell to provide a distribution of HER2 copy number heterogeneity. 1000 pieces of data were created, representing an initial tumor cell population similar to the cell population of the analyzed Images. In other words, from the extracted tumor cell data a plurality of pieces of data corresponding to cells of the tumor each with a degree of activation of HER2 is provided. In addition, each piece of data is attributed a spatial localization in a three-dimensional space representing the tumor.

Figure 5A:
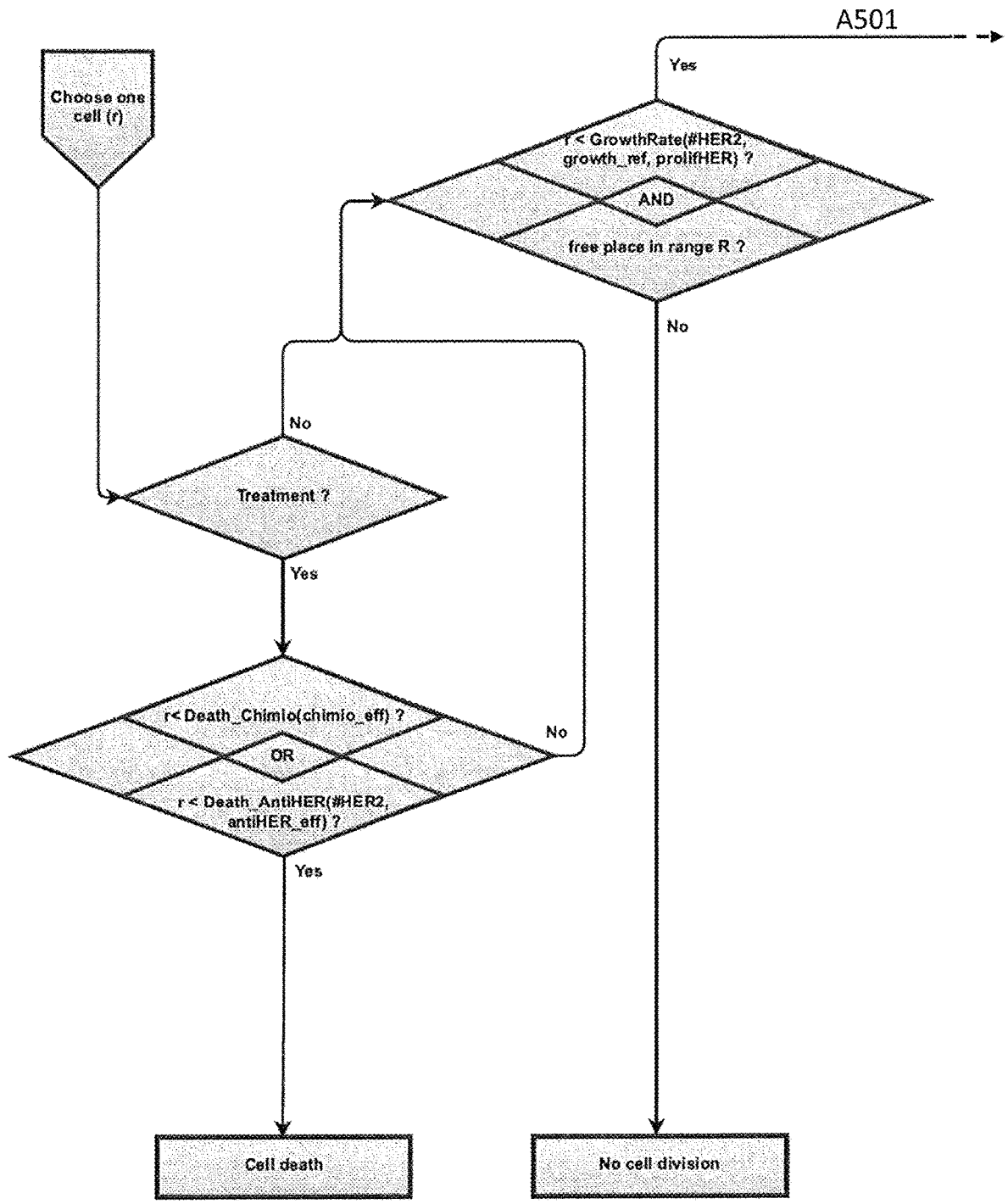
FIGS. 5A and 5B show a flowchart of an example of a model of the method.
Figure 5B:
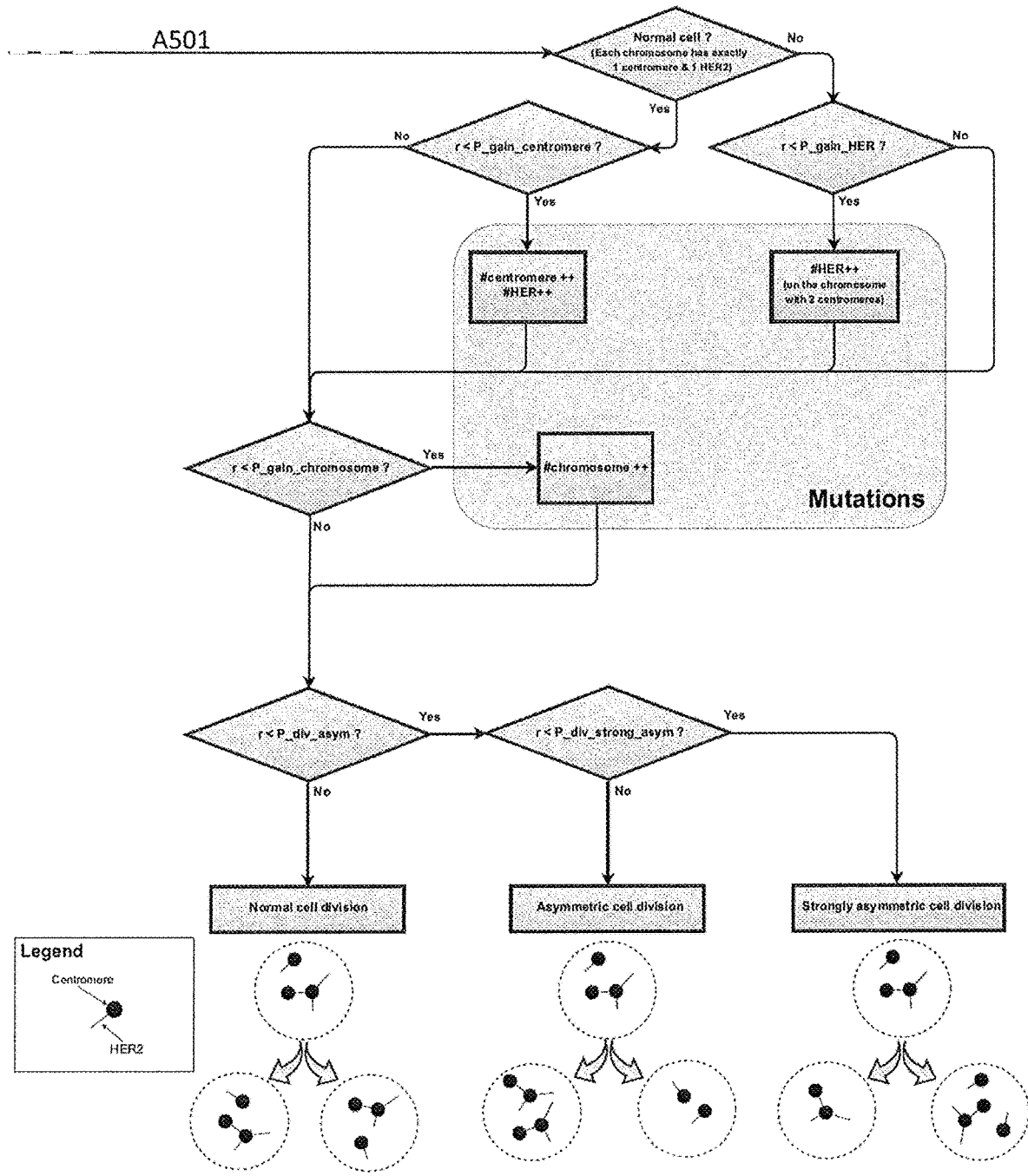

FIG. 5A and FIG. 5B show respective portions of an example of the model. The portion represented on FIG. 5A is connected to the portion represented on FIG. 5B by arrow A501. In this example, the model is specific to one or more oncogenes. The model is based on biological knowledge, of oncogene activation genetic mechanisms (such as gene amplification, fusion, mutation). The model is further based on oncogene functional effects on core cellular pathways (such as cell growth, cell division, apoptosis, paracrine secretion). For HER2 gene amplification, the model takes into account:
- cell division rate, depending on the oncogenes status (i.e. HER2 amplification levels);
- cell death rate, which may depend on the treatment type (such as chemotherapy and anti-HER2 antibodies);
- the probability of Breakage-Fusion-Bridge event [20, 21, 22, 5], (such as break at telomeric side HER2 gene), leading to a di-centric chromosome 17 and that initiate the HER2 amplification (initiation event);
- the probability of Breakage-Fusion-Bridge, only when a di-centric chromosome 17 is present (extension event);
- the probability of unbalanced mitotic chromosome segregation, increased by di-centric chromosome, leading to asymmetric division.

The model is configured to simulate the evolution of a tumor through asynchronous cellular automation. Individual cells are updated independently, in such a way that the new state of a cell affects the calculation of states in neighboring cells, and in which cell events are stochastically driven using a decision-tree model.

Figure 6:
FIG. 6 shows an example of a GUI for inputting data relative to the patient.

Referring now to FIG. 6, clinical data and genomic data of a patient are used to identify the model parameters values in a patient individualized manner. FIG. 6 shows an example of a GUI on which data relative to the patient may be inputted. The data relative to the patient may further be stored and retrieved from a database. From the data relative to the patient, the values of the parameters of the model are adjusted.

In this example, the model further takes into account three treatment types for advanced HER2 breast cancer: chemotherapy (such as paclitaxel), anti-HER2 therapy (such as TDM-1 Trastuzumab-Ado-Emtensine) and a combination of both chemotherapy and anti-HER2 (such as Trastuzumab+pertuzumab+paclitaxel). The three treatment types may be modeled depending on their mechanism of action. Each treatment type may be computed as a vector returning a value for each mechanism of action the treatment type comprises.

Each treatment has its own way of action. Chemotherapy is a non-selective treatment. It kills cells independently of their state and their nature. Chemotherapy may be modeled by the following probability function:

$$\text{Death\_chimio}(chimio_{\mathit{eff}}) = \frac{chimio\_eff}{1 + chimio\_eff}$$

where chimio_eff is the efficacy of the chemotherapy.

Anti-HER2 therapy is a targeted therapy that is more efficient if there are more HER2 copies in the cells. This phenomenon may be modelled through a probability function such as the following Death_AntiHER probability function:

$$\text{Death\_AntiHER}(\#HER, \beta) = \max\left(0, \frac{\beta(\#HER - 2)}{1 + \beta|\#HER - 2|}\right)$$

where:
β is a positive parameter;
HER is the degree of activation of HER2 and depends on the number of HER2 copies. If #HER2 is lower than two, the probability of death is zero.

Alternatively, a probability function as known in the art may be selected.

Back to FIG. 5A, once the model is initialized a cell corresponding to a piece of data is randomly selected and the decision tree is applied with random values "r", linearly distributed between 0 and 1, at each decision. The values of r are compared with the probability associated to the decision and an outcome is selected accordingly.

The cell passes through different decision steps. First a decision on the survival of the cell is computed based on the effect of a treatment which induces cell death. If the cell dies, a new cell is selected at random. If the cell survives, a new decision on whether the cell divides or not is taken.

The probability for a cell to divide depends on the cell's growth rate which may be modeled using 3 parameters determined by a combination of a covariable model, prior biological knowledge and a replay of the history of the tumor. An exemplary probability function which may model growth rate is presented below:

$$GrowthRate(\#HER, \gamma_0, \alpha) = \frac{Ce^{\alpha(\#HER-2)}}{1 + Ce^{\alpha(\#HER-2)}}$$

$$\text{with } C = \frac{\gamma_0}{1 - \gamma_0}$$

where:
$\gamma_0$ is comprised between 0 and 1 and is a reference growth rate;
$\alpha$ is a parameter which modulates growth rate depending on the intensity of #HER2 and depends on the patient;
HER2 is the degree of activation of HER2.

Furthermore, a verification on space availability is performed around a range R from the spatial localization of the cell. The parameter R may be fixed during the initialization of the model and corresponds to a distance from the spatial localization of the cell. Only if the random draw r is lower than the value given by the GrowthRate function and there is an available spatial localization for a new cell resulting from division does the cell undergoes division. In such a case the path of arrow A501 is followed and continues on FIG. 5B. The space localization of the two cells which will result from the cell division may be determined at this step. If any one of the two conditions for cell division is not satisfied, there is no division and a new cell is selected at random.

Now referring to FIG. 5B, after determining the cell undergoes division, the path of arrow A501 is followed. Next a verification is performed on the degree of activation of HER2 inside the cell. The verification may comprise whether each chromosome of the cell has exactly 1 centromere and 1 copy of HER2. If this is the case, the probability for a cell to have an initiation event around HER2 (a double strand DNA break followed by a breakage-fusion-bridge (BFB)) is computed. This is also referred as gaining a centromere. The probability to gain a centromere may be modeled by a function called P_gain_centromere. The probability function may be modeled from a mixed non-linear model taking as covariables data relative to the patient, such as the BMI index, age [25] and smoking and genetic risk factors [26]; such as mutations on FGFR2: rs2981579 and FGFR2:2981582. An example of the logarithm of the function is presented below:

Log($P\_gain\_centromere_j$)=Log($P\_gain\_ceontromere_{basal}$)+$p \times COV_j$+$\eta_j$ With:
$P\_gain\_ceontromere_{basal}$ an average probability to gain a centromere.

$$-p = \begin{pmatrix} p_1 \\ p_2 \\ p_3 \\ p_4 \end{pmatrix}^t$$

weight parameters;

$$\% \text{ of tumor evolution} = \frac{\text{(final number of cells} - \text{initial number of cells)}}{\text{initial number of cells}}$$

a covariance matrix taking into account the BMI index, the age and two genetic risk factors of the patient FGFR2: rs2981579 and FGFR2:2981582.

$\eta_j \sim \mathcal{N}(0, P\_gain\_ceontromere_{basal} \times \omega^2)$ with $\omega^2(\approx 0.01)$ a random noise taking into account the variability of biological mechanisms.

If the cell already has more than 1 centromere or more than one HER2 copy on at least one chromosome, then instead of computing the probability to gain an initiation event around HER2 the probability for a dicentric cell to have a BFB extension event is computed. The probability for a dicentric cell to have a BFB extension event may be modeled similarly to the probability to gain an initiation event around HER2. The computation may be performed by comparing the result of a random value r against the modeled probability.

Next, a computation is performed to determine if the cell gains an additional chromosome, in addition to the replicated chromosomes appearing during cell division. If the cell gains an additional chromosome, the degree of activation of HER2 increases significantly.

Next the probability for a cell to have unbalanced chromosome segregation, resulting in asymmetric division is computed. Normal cell division is symmetric, in which case the two cells resulting from the division have the same degree of HER2 activation. However, cells may divide asymmetrically resulting in a difference between the degree of HER activation between the two cells resulting from the division. In the example shown in FIG. 5B, the first cell resulting from asymmetric cell division has two centromeres and three HER2 copies per chromosome. The second cell resulting from asymmetric cell division has only one copy of HER2 and one centromere per chromosome. The determination of the presence or absence of asymmetric cell division may be computed similarly to the determination of gaining an additional chromosome. If the cell undergoes asymmetric cell division, a second computation may determine if the asymmetric cell division is strong or not. A strong asymmetric cell division is an asymmetric cell division where the number of chromosomes between the two cells resulting from division is unbalanced. In the example of FIG. 5B the first cell resulting from strongly asymmetric cell division has three chromosomes while the second cell has only one. The computation determining the presence of strong asymmetric cell division may be performed similarly to the presence of asymmetric cell division.

After a cell divides, two new cells are created. Each cell corresponding to a respective piece of data. One of the respective pieces of data may replace the piece of data corresponding to the cell which underwent the decision tree. The other piece of data may be created after the run. The plurality of pieces of data may be updated with the result from the decision tree after each run. Alternatively, the plurality of pieces of data may be updated after all the cells corresponding to the plurality of pieces of data have gone through the decision tree. The determination of space availability may take into account the new cells resulting from cell division, even if the plurality of pieces of data have not been updated yet.

After all the cells have gone through the decision tree, a new iteration of the model may be performed with the updated plurality of pieces of data.

Figure 7:
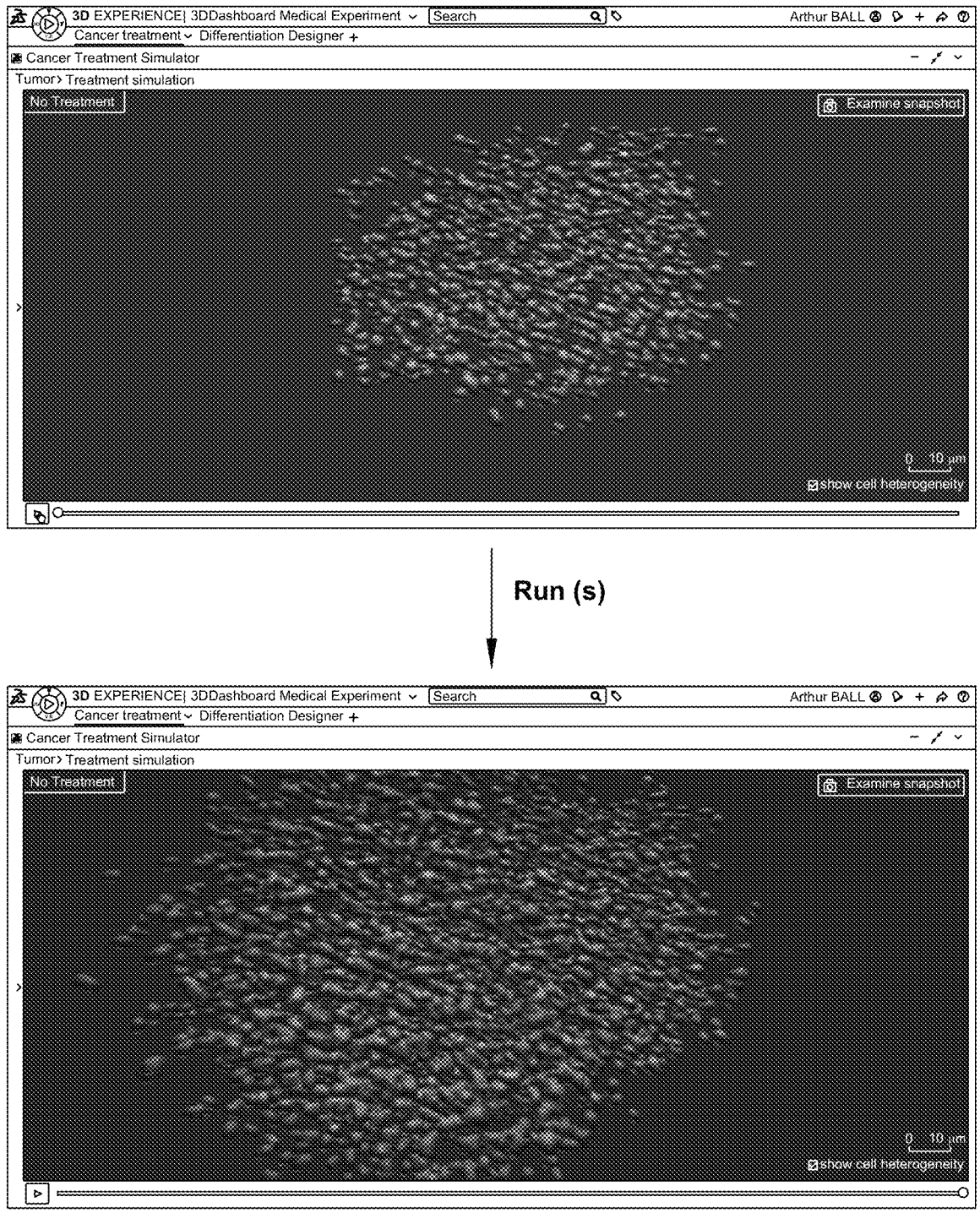
FIG. 7 shows an example of the simulated tumor.

FIG. 7 shows an example of the spatial representation of the cells corresponding to the plurality of pieces of data before going through the model and after going through one or more runs of the model. Through differences in intensity and color, the degree of HER2 activation in the cells may also be represented. Alternatively other methods to distinguish the degree of oncogene activation in the cells may be used when computing a representation of the cells in their respective spatial localizations. The spatial representation of the cells after going through the model is a simulation on how the tumor will evolve from its initial state to a final state. The final state depends on the data extracted from the cells used to create the initial plurality of pieces of data, as well as the data relative to the patient and/or the type of treatment. Spatial representations may be computed after each run of the model, so that a real time evolution of the tumor may be visualized by a user. Such a visual representation may be directly interpreted by pathologists for histological analysis.

Figure 8:
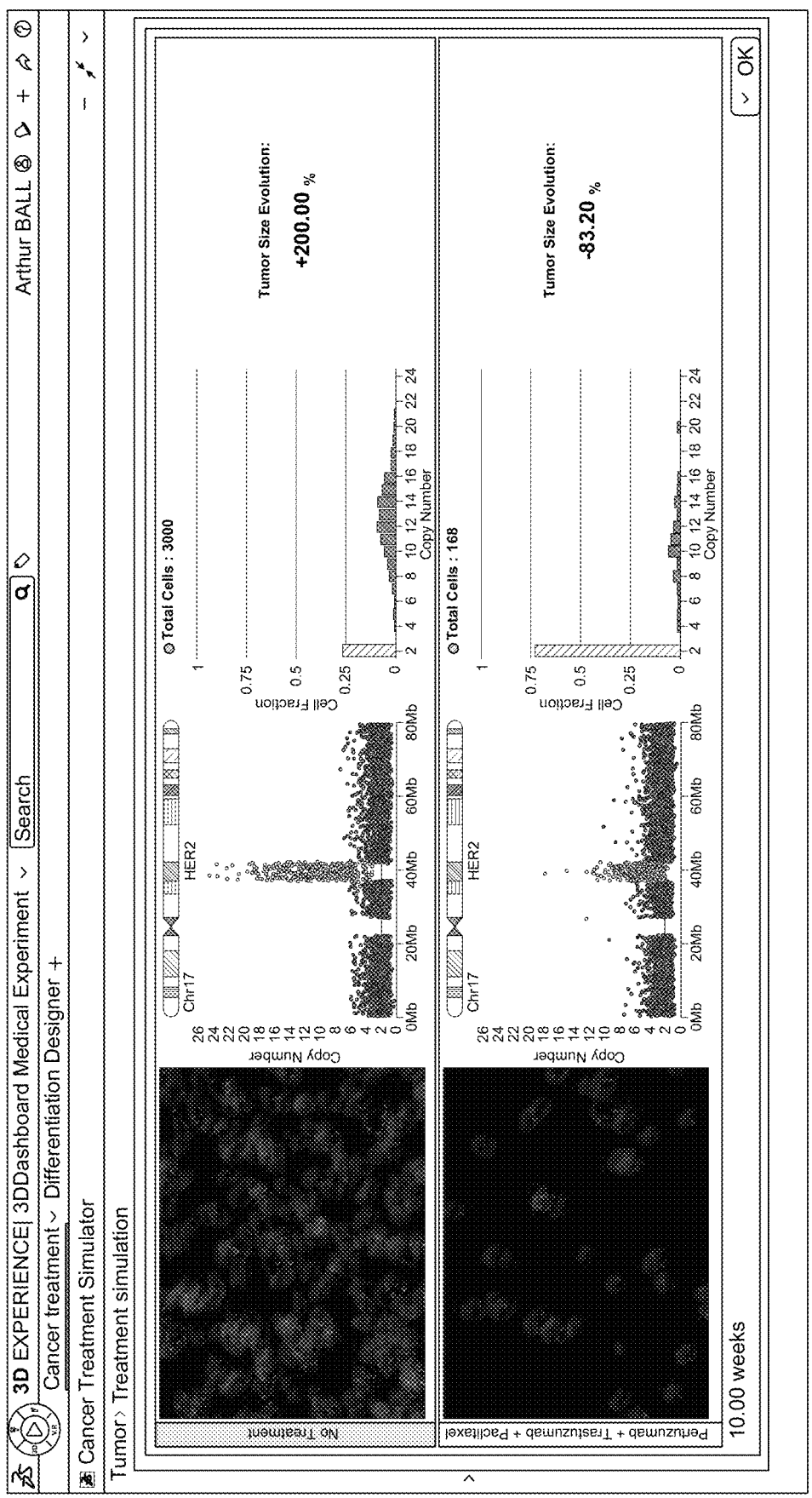
FIG. 8-9 show an example of statistics computed from the model.

Referring now to FIG. 8, alternatively or additionally, a copy number plot may be computed from the updated plurality of pieces of data, as if the tumor has been sequenced and then analyzed. The plot may correspond to the entire updated plurality of pieces of data. Alternatively, the plot may correspond to a part of the plurality of pieces of data, such as the pieces of data corresponding to the cells located in a two-dimensional plane going through the simulated tumor. The mean copy number among cells and a confidence interval for the noise distribution may be further computed. A histogram plot of the HER2 copy number distribution in the total cell population may be further presented to the user, such as the one shown in FIG. 8. Computing such statistics facilitates the interpretation of the results by geneticist, as genetic information extracted from the simulation is presented in a similar format as a genomics analysis.

Figure 9:
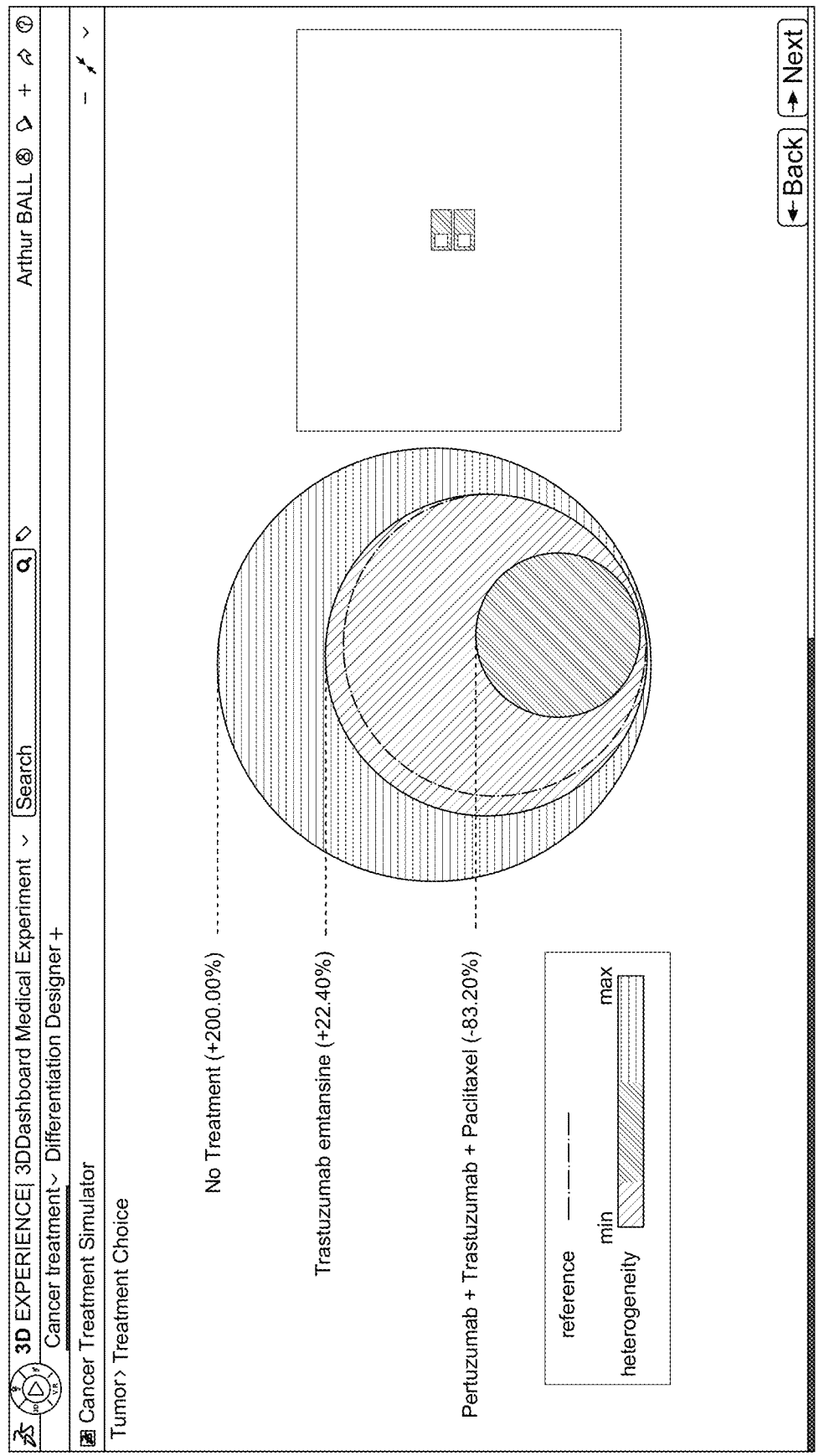

Referring now to FIG. 9, alternatively or additionally, a percentage of tumor evolution may be computed based on the following formula:

$$-COV_j = \begin{pmatrix} BMI_j \\ age_j \\ FGFR2:rs2981579j \\ FGFR2:2981582j \end{pmatrix}$$

This computation facilitates the comparison of tumor evolution with other similar cases. Additionally, several simulations for the same tumor may be simultaneously presented to the user. For example, simulations resulting from different treatment combinations each showing the percentage of tumor evolution when compared to the initial tumor size (dashed line). Additionally, from the degree of activation of HER2 in the cells, a comparative value of intra-tumor heterogeneity may be computed and presented to the user. These computations facilitate the interpretation of the results of the simulation by oncologists, as they are similar to RECIST criteria. The RECIST criteria only allows to follow the evolution of the volume of a tumor but does not provide information on the heterogeneity of the tumor. The method further provides information on the evolution of the heterogeneity of the tumor.

Additionally, the method for simulating the evolution of a tumor may be performed with the degree of activation of HER2 and one or more other oncogenes also present in breast cancer. In such cases, the values of the parameters of the model may depend on the one or more oncogenes similarly to how the parameters depend on HER2 in the above example.

Figure 11:
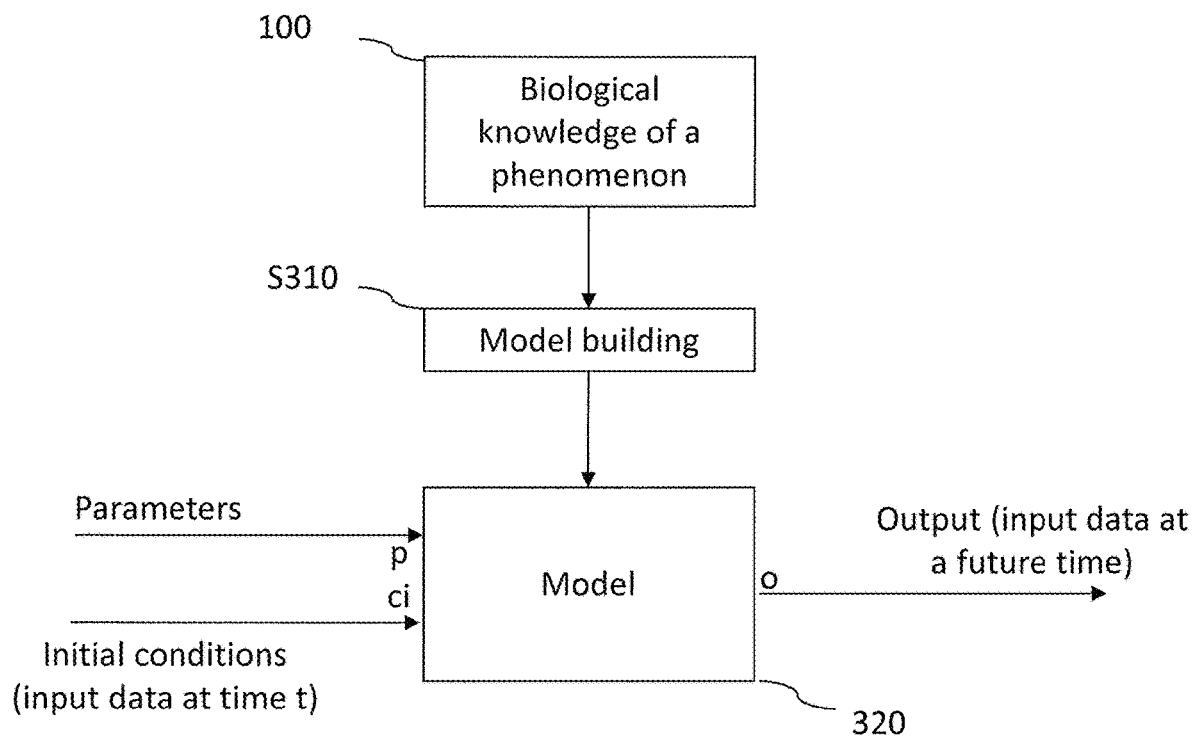
FIG. 11 shows a flowchart of the data flow of an example of the model.

FIG. 11 is an example of model building and data flow for an example of the model of the method for simulating the evolution of a tumor. From biological knowledge (100) of a phenomenon related to the tumor, a model (320) may be built (S310). Parameters and initial conditions are injected into the model and output data. The in parameters and/or initial conditions may be the input data of the model at a given time t. The output data may correspond to an evolution of the input data in time, that is the input data at a future time t+t'.

Figure 12:
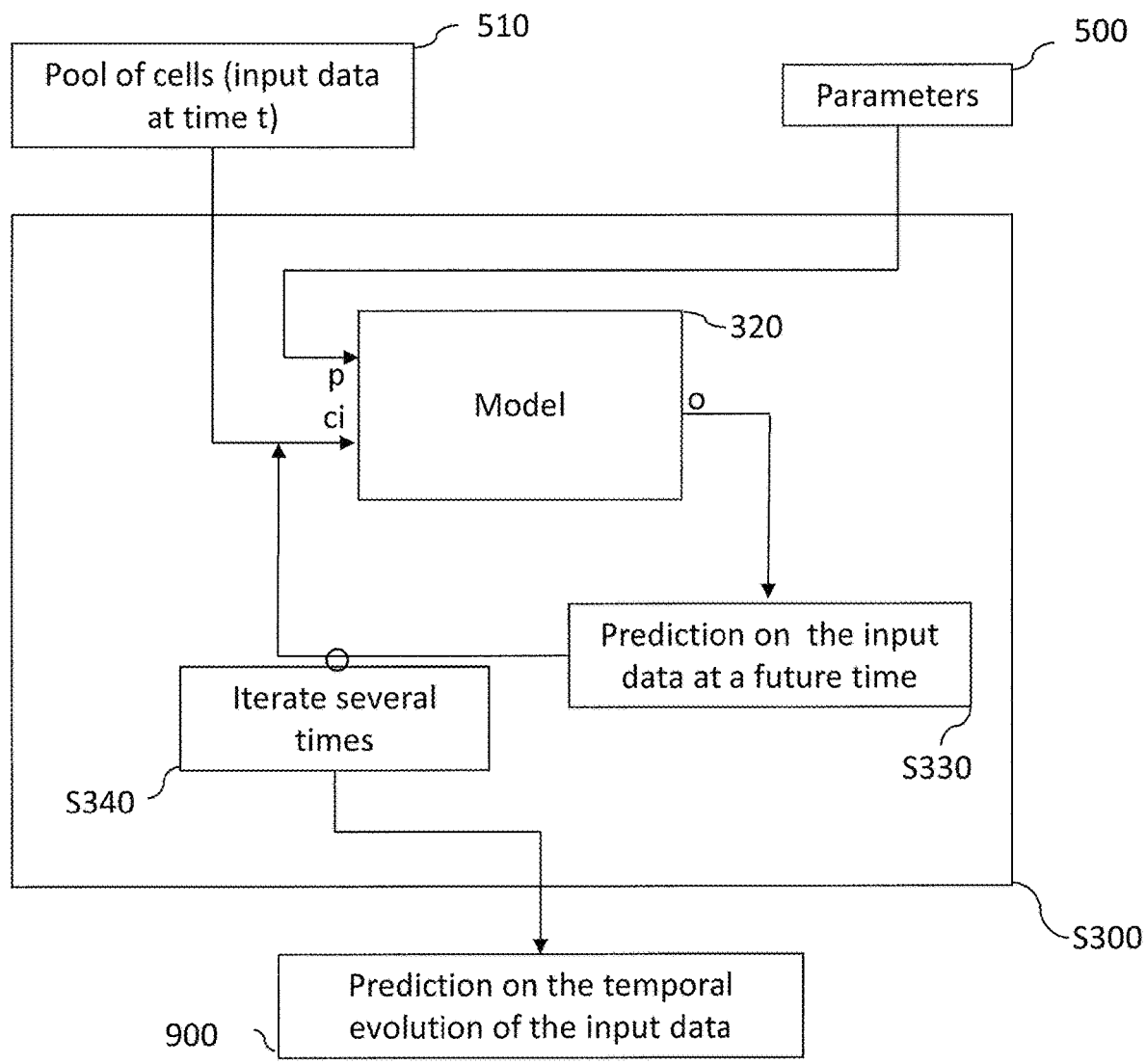
FIG. 12 shows a flowchart of the dataflow of an example of the model comprising several iterations.

FIG. 12 is an example of a model outputting a prediction on the temporal evolution of the input data (900) for the simulation of the evolution of a tumor. The input data (510) represents a pool of cells, for example, the input data may be pieces of data each representing a tumor cell. Parameters (500) are injected into the model for the simulation. The model is run (S300). The run may comprise iterating (S340) several times the input-output from the model (320). At each iteration the model outputs (S330) a prediction on the input data at a future time. For example, after each iteration, the temporal evolution of the pool of cells may advance in time for a duration equal to a cell cycle. Alternatively, the pool of cells may advance in time for a duration of a fraction of a cell cycle depending on the input data. After several iterations, a prediction on the temporal evolution of the input data may be computed.

Figure 13:
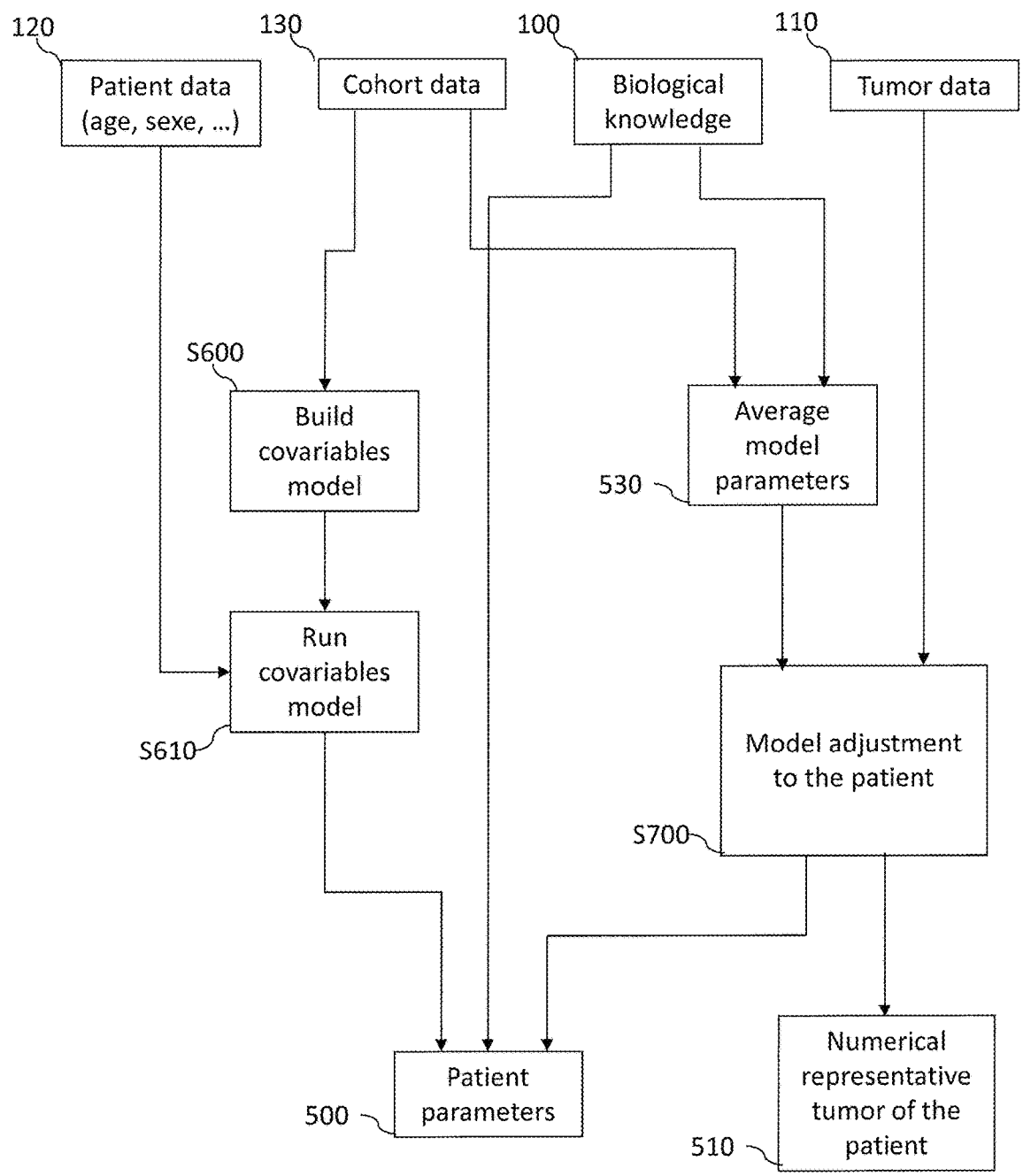
FIG. 13 shows a flowchart of an example of determining input and parameters for the model.

FIG. 13 is an example illustrating the adjustment of parameters of the model for a given patient (patient parameters). The patient parameters (500) are adjusted from a combination or any one of data relative to the patient (120), cohort data (130), biological knowledge (100) and tumor data (110). In other examples any one of or a combination of data relative to the patient, cohort data, biological knowledge and tumor data may be used to determine the patient parameters. Cohort data may be data from other patients which have a similar tumor as the patient. From the cohort data, a covariable model may be built (S600) as known in the literature. The covariable model may be run (S610) on the data relative to the patient (120) which may determine patient parameters. The patient parameters may also be adjusted from biological knowledge (100), for example, data from the literature. The cohort data (130) and the biological knowledge (100) may be combined to create average model parameters (530). These average model parameters represent parameters of the model which are adjusted for an average member of a population. The average model parameters are injected in the model adjustment (700). Tumor data (100), such as data extracted from a biological image of the tumor of the patient may be used to compare the output data from model runs where the model is parametrized with the average model parameters, in order to adjust (S700) the model to the patient as previously discussed. The patient parameters (500) may be further adjusted with the runs of the model. The model may then output numerical data representative of the tumor of the patient (510).

Figure 14:
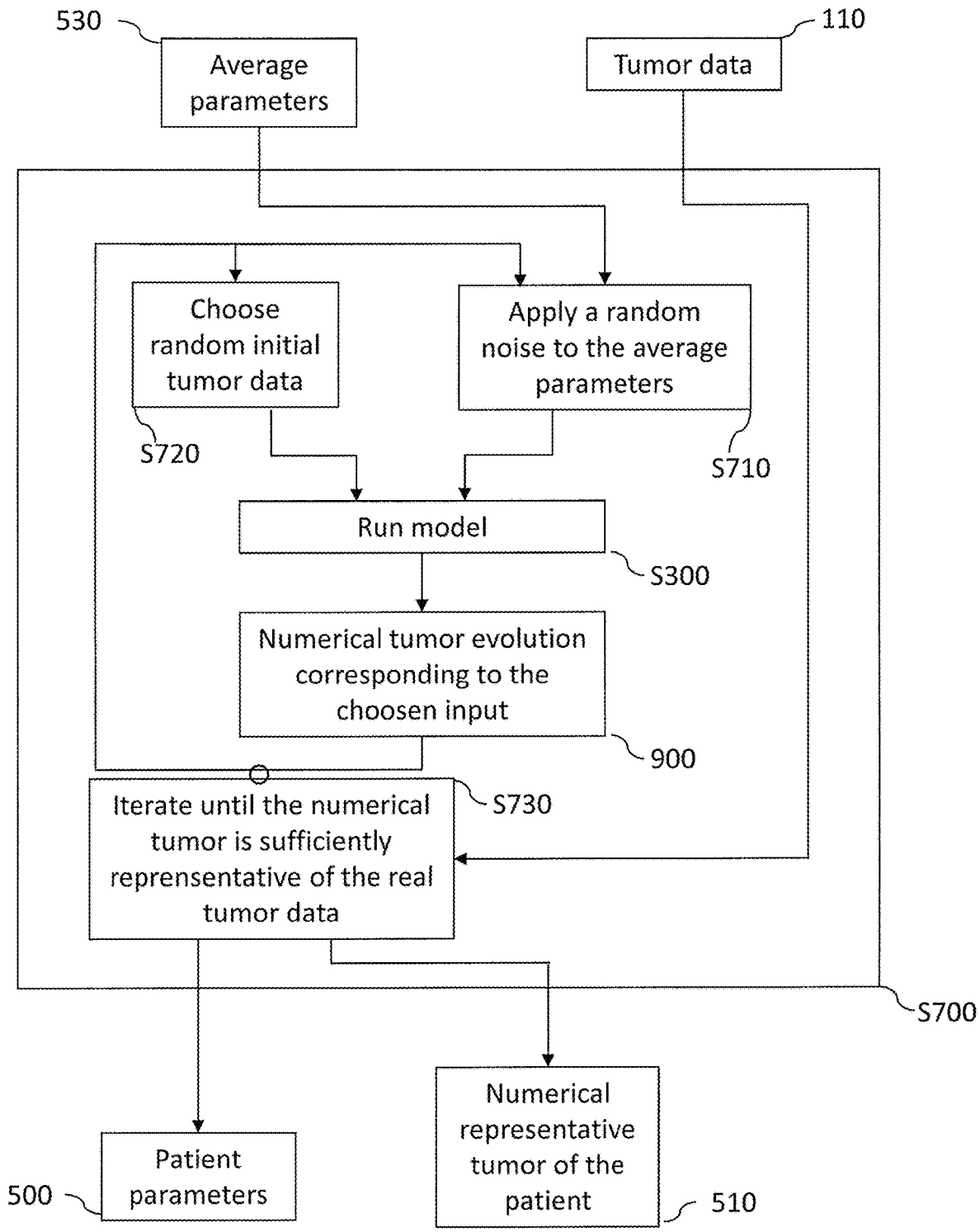
FIG. 14 shows a flowchart of an example of computing personalized parameters of the model for a patient.

FIG. 14 is an example of the model adjustment at S700. In the model adjustment, a random noise may be applied (S710) to the average parameters (530) before they are injected in the model. Random initial tumor data is computed (S720) as input data and the model is run (S300). A numerical tumor evolution (900) corresponding to the choice of parameters and input data is outputted. The model may be run again on the outputted data for several iterations before being compared to tumor data of the patient, such as data extracted from an image of the tumor of the patient. The computation of random initial tumor data and application of random noise to the average parameters and subsequent model runs is iterated (S730) until the numerical tumor is sufficiently representative of the real tumor data. The parameters of the model, from which the numerical tumor sufficiently representative of the real tumor data was computed, may then become the patient parameters (500) and the model may output numerical data representative of the tumor of the patient (510) as the parameters are now personalized to the patient.

The invention claimed is:

1. A computer-implemented method for assisting determining a treatment to be administered to a patient having a tumor, the method comprising:
   obtaining a plurality of treatment types, the plurality of treatment types comprising one or more targeted treatments, one or more general treatments and/or one or more combinations of targeted treatments and/or general treatments;
   for each treatment type of the plurality:
      simulating, taking into account the type of treatment, evolution of the tumor associated with an oncogene, the simulating including:
         obtaining a plurality of pieces of data each corresponding to a given cell of the tumor, each piece of data including a degree of activation of an oncogene in the given cell and obtaining a model configured to take as an input one of the pieces of data and to output information related to proliferation of the respective given cell corresponding to the input one of the pieces of data, the information on proliferation depending on the degree of activation of the oncogene in the respective given cell and on the treatment type,
         wherein the model is decision-based and includes, relative to the respective given cell:
            a decision on death or survival,
            a decision on absence or presence of division, and
            a decision on acquisition of one or more new alterations during a division, and
         wherein the model is further configured to take into account the treatment type when determining if a cell corresponding to a piece of data taken as input survives;
         running the model on one or more pieces of data of the plurality of pieces of data; and
         updating the plurality of pieces of data based on the result of the running; and
      computing a percentage of tumor evolution based on the evolution simulated for the treatment type; and
   outputting information on the evolution of the tumor simulated for each treatment type including the computed percentage of tumor evolution.

2. The method of claim 1, wherein each piece of data further includes a localization of the given cell of the tumor.

3. The method of claim 2, wherein:
   the information on proliferation of the respective given cell includes a piece of information indicating presence or absence of division of the respective given cell, and
   when the information on proliferation of the respective given cell includes information relative to the presence of division, the presence of division resulting in child cells, the information on proliferation of the respective given cell further includes, for each child cell resulting from the division, an information on a respective localization, each respective localization being in a neighborhood of the localization of the respective given cell.

4. The method of claim 3, wherein the information on proliferation of the respective given cell further depends on space availability in the neighborhood of the respective given cell.

5. The method of claim 4, wherein:
   the information indicating presence or absence of division of the respective given cell is based on the space availability in the neighborhood of the respective given cell, and
   when the information on proliferation of the respective given cell includes information relative to presence of division, the respective localization in the neighborhood of the localization of the respective given cell is at an unoccupied localization.

6. The method of claim 5, wherein, when the information on proliferation of the respective given cell includes information indicating the presence of division, the information on proliferation of the respective given cell further includes for each child cell resulting from the division, a respective degree of activation of the oncogene, based on the degree of activation of the oncogene of the respective given cell.

7. The method of claim 6, wherein the respective degree of activation of the oncogene of each child cell resulting from the division corresponds to an at least partly probabilistic variation of the degree of activation of the oncogene of the respective given cell.

8. The method of claim 1, further comprising obtaining data relative to a patient having the tumor, the model including parameters that depend on the data relative to the patient.

9. The method of claim 8, wherein the obtaining the model includes determining the parameters as values configured for retrieving the plurality of pieces of data by:
   defining one or more other pieces of data, each other piece of data corresponding to a given cell of an initial state of the tumor, each other piece of data including a degree of activation of the oncogene in the given cell,
   running the model on one or more other pieces of data, and
   updating the one or more other pieces of data based on the result of the running,
   wherein optionally the parameters as values are initialized based on the data relative to the patient.

10. The method of claim 1, further comprising determining a statistic relative to the oncogene, based on the updated plurality of pieces of data.

11. The method of claim 1, further comprising:
   performing or adapting therapy of a patient using the updated plurality of pieces of data.

12. A non-transitory data storage medium having stored thereon a data structure including a model and a computer-implemented method for assisting determining a treatment to be administered to a patient having a tumor, the method comprising:
   obtaining a plurality of treatment types, the plurality of treatment types comprising one or more targeted treatments, one or more general treatments and/or one or more combinations of targeted treatments and/or general treatments;
   for each treatment type of the plurality:
      simulating, taking into account the type of treatment, evolution of the tumor associated with an oncogene, the simulating including:
         obtaining a plurality of pieces of data each corresponding to a given cell of the tumor, each piece of data including a degree of activation of an oncogene in the given cell and obtaining a model configured to take as an input one of the pieces of data and to output information related to proliferation of the respective given cell corresponding to the input one of the pieces of data, the information on proliferation depending on the degree of activation of the oncogene in the respective given cell and on the treatment type, wherein the model is decision-based and includes, relative to the respective given cell:
a decision on death or survival,
a decision on absence or presence of division, and
a decision on acquisition of one or more new alterations during a division, and wherein the model is further configured to take into account the treatment type when determining if a cell corresponding to a piece of data taken as input survives;

running the model on one or more pieces of data of the plurality of pieces of data; and updating the plurality of pieces of data based on the result of the running; and computing a percentage of tumor evolution based on the evolution simulated for the treatment type; and outputting information on the evolution of the tumor simulated for each treatment type including the computed percentage of tumor evolution.

13. A non-transitory data storage medium having stored thereon a computer program, the computer program comprising instructions configured for performing a computer-implemented method for assisting determining a treatment to be administered to a patient having a tumor, the method comprising:

obtaining a plurality of treatment types, the plurality of treatment types comprising one or more targeted treatments, one or more general treatments and/or one or more combinations of targeted treatments and/or general treatments;

for each treatment type of the plurality:
simulating, taking into account the type of treatment, evolution of the tumor associated with an oncogene, the simulating including:
obtaining a plurality of pieces of data each corresponding to a given cell of the tumor, each piece of data including a degree of activation of an oncogene in the given cell and obtaining a model configured to take as an input one of the pieces of data and to output information related to proliferation of the respective given cell corresponding to the input one of the pieces of data, the information on proliferation depending on the degree of activation of the oncogene in the respective given cell and on the treatment type, wherein the model is decision-based and includes, relative to the respective given cell:
a decision on death or survival,
a decision on absence or presence of division, and
a decision on acquisition of one or more new alterations during a division, and wherein the model is further configured to take into account the treatment type when determining if a cell corresponding to a piece of data taken as input survives;

running the model on one or more pieces of data of the plurality of pieces of data; and updating the plurality of pieces of data based on the result of the running; and computing a percentage of tumor evolution based on the evolution simulated for the treatment type; and outputting information on the evolution of the tumor simulated for each treatment type including the computed percentage of tumor evolution.

14. A system comprising:

a processor; and a memory, the memory having recorded thereon a computer program, including instructions for assisting determining a treatment to be administered to a patient having a tumor configured so that when executed by the processor, the program causes the processor to be configured to:

obtain a plurality of treatment types, the plurality of treatment types comprising one or more targeted treatments, one or more general treatments and/or one or more combinations of targeted treatments and/or general treatments;

for each treatment type of the plurality:
simulate, taking into account the type of treatment, evolution of the tumor associated with an oncogene, the processor being further configured to simulate the evolution by being further configured to:
obtain a plurality of pieces of data each corresponding to a given cell of the tumor, each piece of data including a degree of activation of an oncogene in the given cell, and obtain a model configured to take as an input one of the pieces of data and to output information related to proliferation of the respective given cell corresponding to the input one of the pieces of data, the information on proliferation depending on the degree of activation of the oncogene in the respective given cell and on the treatment type, wherein the model is decision-based and includes, relative to the respective given cell:
a decision on death or survival,
a decision on absence or presence of division, and
a decision on acquisition of one or more new alterations during a division, and wherein the model is further configured to take into account the treatment type when determining if a cell corresponding to a piece of data taken as input survives, run the model on one or more pieces of data of the plurality of pieces of data, and update the plurality of pieces of data based on the result of the running, and compute a percentage of tumor evolution based on the evolution simulated for the treatment type, and output information on the evolution of the tumor simulated for each treatment type including the computed percentage of tumor evolution.

\* \* \* \* \*